US009133208B2

(12) United States Patent
Wei et al.

(10) Patent No.: US 9,133,208 B2
(45) Date of Patent: Sep. 15, 2015

(54) RADIOLABELLED ROTENONE DERIVATIVES AND THEIR USE IN SPECT IMAGING

(75) Inventors: Lihui Wei, Kanata (CA); Xuxu Yan, Palm Beach Gardens, FL (US); Corinne Bensimon, Nepean (CA); Terrence David Ruddy, Nepean (CA)

(73) Assignee: NORDION (CANADA) INC., Ontario (CA)

( * ) Notice: Subject to any disclaimer, the term of this patent is extended or adjusted under 35 U.S.C. 154(b) by 426 days.

(21) Appl. No.: 13/549,093

(22) Filed: Jul. 13, 2012

(65) Prior Publication Data

US 2013/0022542 A1 Jan. 24, 2013

Related U.S. Application Data

(60) Provisional application No. 61/507,291, filed on Jul. 13, 2011.

(51) Int. Cl.
*A61K 51/00* (2006.01)
*A61M 36/14* (2006.01)
*C07D 493/14* (2006.01)

(52) U.S. Cl.
CPC .................................. *C07D 493/14* (2013.01)

(58) Field of Classification Search
None
See application file for complete search history.

(56) References Cited

U.S. PATENT DOCUMENTS

2009/0136424 A1   5/2009   Van Brocklin et al.
2010/0021378 A1*  1/2010   Rousso et al. ............... 424/1.11

FOREIGN PATENT DOCUMENTS

WO   WO 2008/133730 A2    11/2008
WO   WO 2008133730 A2 *   11/2008

OTHER PUBLICATIONS

Martarello et al. J. Labelled Cpd. Radiopharm. 1999, 1039-1051.*
Krummeich et al. Appl. Radiat. Isot. 1996, 489-495.*
Crombie et al. J. Chem. Soc. Perkin Trans. 11991, 3143-3148.*
Morin Tetrahedron Lett. 2006, 47, 5055-5058.*
Alexis Broisat et al., Myocardial Uptake of 7'-(Z)-[$^{123}$I]Iodorotenone During Vasodilator Stress in Dogs With Critical Coronary Stenoses, Circulatory Cardiovasc Imaging, vol. 4, pp. 685-692, 2011.
Christopher P. Reinhart et al., Stable Labeled Microspheres to Measure Perfusion: Validation of a Neutron Activation Assay Technique, American Journal Physiology Heart Circulatory Physiology, vol. 280, pp. H108-H116, 2001.
David K. Glover et al., Comparison Between $^{201}$Tl and 99$^m$Tc Sestamibi Uptake During Adenosine-Induced Vasodilation as a Function of Coronary Stenosis Severity, Circulation, vol. 91, pp. 813-820, 1995.
Robert C. Marshall et al., Kinetic Analysis of $^{125}$I-Iodorotenone as a Deposited Myocardial Flow Tracer: Comparison with $^{99m}$Tc-Sestamibi, The Jounal of Nuclear Medicine, vol. 42, No. 2. pp. 272-281, Feb. 2001.
Robert C. Marshall et al., Kinetic Analysis of $^{18}$F-Fluorodihydrorotenone as a Deposited Myocardial Flow Tracer: Comparison to $^{201}$Tl, The Journal of Nuclear Medicine, 2004, vol. 45, No. 11, pp. 1950-1959.

\* cited by examiner

*Primary Examiner* — Michael G Hartley
*Assistant Examiner* — Sean R Donohue
(74) *Attorney, Agent, or Firm* — Arent Fox LLP

(57) ABSTRACT

The present application discloses a compound of formula (I) or (II):

wherein X is gamma-emitting radionuclide. Also disclosed is a pharmaceutical composition comprising the compound of formula (I), the compound of formula (II), or a mixture thereof, and a physiologically acceptable vehicle and a method of imaging a region in a patient, which includes administering to the patient a diagnostically effective amount of the pharmaceutical composition comprising the compound of formula (I), the compound of formula (II), or a mixture thereof.

30 Claims, 19 Drawing Sheets

RADIOLABELLED ROTENONE DERIVATIVES AND THEIR USE IN SPECT IMAGING

CROSS-REFERENCE TO RELATED APPLICATIONS

This nonprovisional application claims the benefit of U.S. Provisional Application No. 61/507,291, filed Jul. 13, 2011, the contents of which are incorporated herein by reference in their entirety.

FIELD OF INVENTION

The present invention provides radiolabelled rotenone derivatives, and methods for their preparation and use in diagnostic imaging. In particular, the present invention provides radio-iodinated rotenone derivatives, methods for their preparation and their use in Single Photon Emission Computed Tomography (SPECT) myocardial perfusion imaging to detect regions of ischemia.

BACKGROUND OF THE INVENTION

Myocardial perfusion imaging is a noninvasive test for assessing the amount of blood flow to the muscle of the heart, and is used in the diagnosis of myocardial ischemia, myocardial infarction, and coronary heart disease. In the test, a nuclear tracer containing a gamma-emitting radionuclide is injected into the blood stream of a patient, and the tracer is taken up by heart muscle cells that receive good blood flow. The heart is then imaged with a camera that detects gamma rays released by the radionuclide of the tracer, thereby providing an image map of blood perfusion or flow to the heart. Two separate scans of the heart are conducted: a first scan where the heart is at rest and a second scan where the heart is under increased workload (i.e. under stress conditions). The two separate scans are compared to assess whether there are any areas in the heart where blood flow is inadequate under stress conditions, which indicates the presence of a blockage or narrowing in the coronary arteries.

Van Brocklin et al. (United States Patent Application Publication No. 2009/0136424) have previously prepared radiolabelled rotenone derivatives for use as myocardial flow tracers based on their ability to localize in the myocardial tissue of the heart. The number of steps required to synthesize these derivatives, however, may preclude their widespread clinical use in myocardial perfusion imaging. There is therefore a need for radiolabelled rotenone derivatives, which can be easily prepared and which demonstrate sufficient stability to be effectively used in myocardial perfusion imaging.

SUMMARY OF THE INVENTION

The present invention provides radiolabelled rotenone derivatives, and methods for their preparation and use in diagnostic imaging. In particular, the present invention provides radio-iodinated rotenone derivatives, methods for their preparation and their use in Single Photon Emission Computed Tomography (SPECT) myocardial perfusion imaging to detect regions of ischemia.

In one aspect, the present invention provides a compound of formula (I) or formula (II):

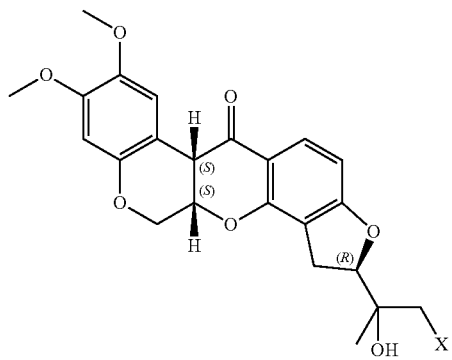

(I)

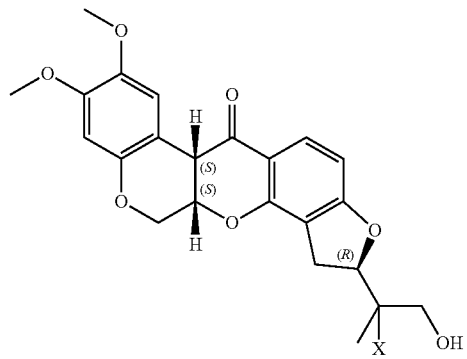

(II)

wherein X is a gamma-emitting radionuclide.

In another aspect, the present invention provides a pharmaceutical composition comprising a compound of formula (I), a compound of formula (II) or a mixture thereof:

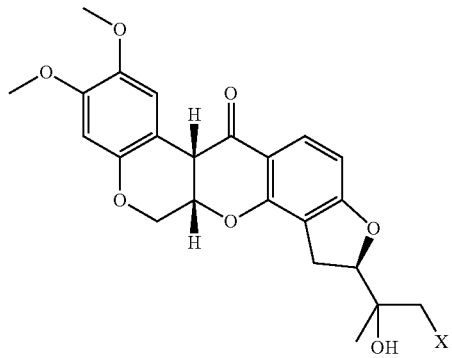

(I)

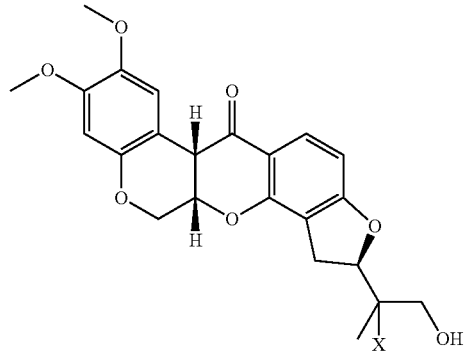

(II)

wherein X is a gamma-emitting radionuclide, and a physiologically acceptable vehicle.

In a further aspect, the present invention provides a method of imaging a region in a patient, comprising:

administering to the patient a diagnostically effective amount of a composition comprising a compound of formula (I), a compound of formula (II) or a mixture thereof:

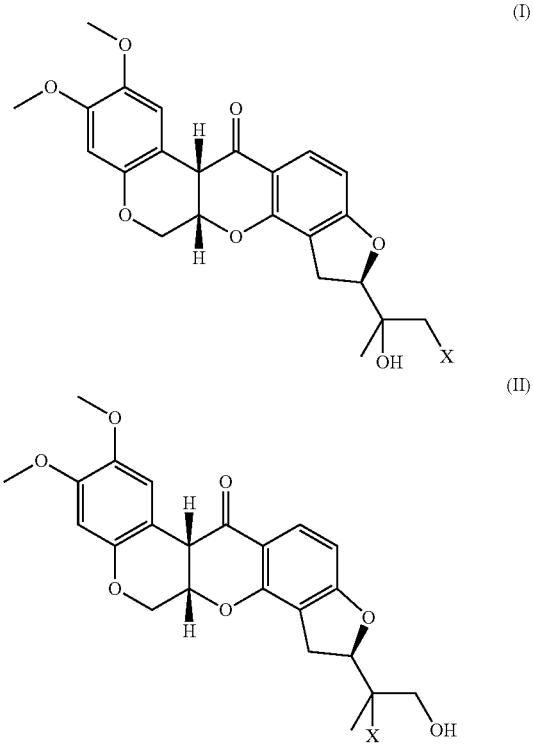

wherein X is a gamma-emitting radionuclide, and a physiologically acceptable vehicle, a portion of the composition being retained in the region of the patient, detecting radiation in the region of the patient, and obtaining an image of the region of the patient.

BRIEF DESCRIPTION OF THE DRAWINGS

These and other features of the invention will become more apparent from the following description in which reference is made to the appended drawings wherein:

FIG. 7 shows polar maps determined by SPECT of the in vivo heart of a pig subject in a resting state and a stressed state, and polar maps representative of the resting and stressed states of the heart of the pig, which were obtained using measurements of gamma radiation emitted from isolated transected sections of the heart of the pig subject. When in the resting state, the pig subject was administered a combination of a mixture of the [$^{123}$I] iodinated rotenone derivatives 6-9 of the present invention and gold BioPal STERIspheres™. In the stressed state, the pig subject was administered a combination of a mixture of the [$^{123}$I] iodinated rotenone derivatives 6-9 of the present invention and samarium BioPal STERIspheres™. Ischemia in the heart of the pig was simulated by constricting the left anterior descending (LAD) coronary artery of the pig.

DETAILED DESCRIPTION OF THE PREFERRED EMBODIMENTS

Figure 1:
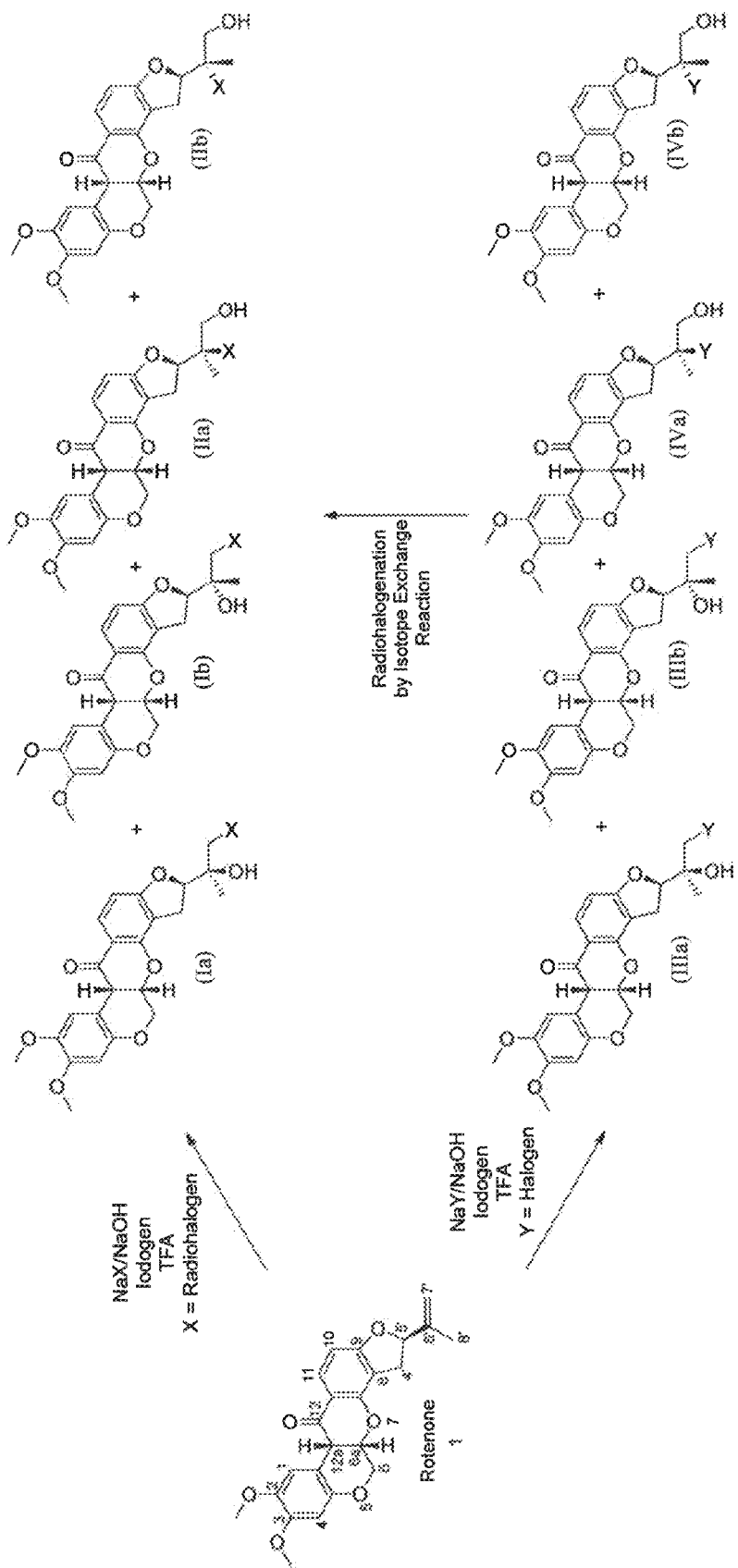
FIG. 1 illustrates examples of synthetic schemes of forming rotenone derivatives according to the present invention.

The present invention provides radiolabelled rotenone derivatives, and methods for their preparation and use in diagnostic imaging. In particular, the present invention provides radio-iodinated rotenone derivatives, methods for their preparation and their use in Single Photon Emission Computed Tomography (SPECT) myocardial perfusion imaging to detect regions of ischemia.

The present invention relates to rotenone derivatives of formula (I) and formula (II):

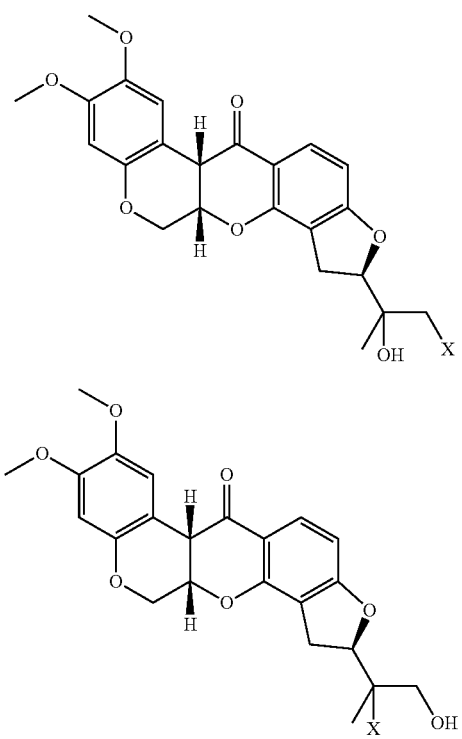

(I)

(II)

wherein X is a gamma-emitting radionuclide, which contain a gamma-radiation emitting radionuclide useful in SPECT imaging. The rotenone derivatives of the present invention have a high affinity to Complex I of the mitochondrial electron transport chain, and can therefore localize in tissues having a high content of mitochondria, such as the myocardium in the heart. In particular, SPECT imaging of blood flow in the heart (myocardial perfusion imaging) using the rotenone derivatives of the present invention can be used to assess the degree of blood flow to the heart and assist in the diagnosis of coronary artery disease in a subject.

Suitable myocardial perfusion imaging studies using the compound of formula (I) and formula (II) can be performed by those of skill in the medical specialty of cardiac imaging (Radiology, Nuclear Medicine and Cardiology) in accordance with generally accepted practices.

Diagnostic compositions of the present invention may be administered by parenteral administration, including but not limited to injection and infusion, either alone or in combination with each other. The compound of formula (I), the compound of formula (II), or a mixture thereof can be administered in the form of a pharmaceutical composition comprising a physiologically acceptable vehicle.

As used herein, the term "physiologically acceptable vehicle" includes, but is not limited to, a carrier medium that does not interfere with the effectiveness of the binding activity of the compound of formula (I) or the compound of formula (II), is chemically inert, and is not toxic to the patient to whom it is administered.

As used herein, the term "effective amount" of the physiologically acceptable vehicle refers to a non-toxic amount of the physiologically acceptable vehicle, which will result in clear imaging of the region of interest of a subject without introducing significant background.

Non-limiting examples of physiologically acceptable vehicles include human serum albumin; aqueous buffer solutions; alcohols, such as ethanol; aqueous alcohol solutions; such as aqueous ethanol; sterile water; physiological saline; sodium chloride injection; Ringer's injection; lactated Ringer's injection; dextrose injection; dextrose and sodium chloride injection; and aqueous solutions containing propylene glycol, polypropylene glycol, a polyethylene glycol (such as polyethylene glycol 300 and polyethylene glycol 400), glycerine, dimethylacetamide (DMA), polyvinyl pyrrolidone (PVP), N-methyl-2-pyrrolidone (NMP), dimethylsulfoxide (DMSO), Polysorbate-80 (Tween 80), Polysorbate-20 (Tween 20), sodium dodecanoate, or hexadecyltrimethyl ammonium bromide. Particular examples of vehicles include aqueous solutions containing propylene glycol (10-68 volume %), ethanol (1-20 volume %), polyethylene glycol 300 (10-50 volume %), polyethylene glycol 400 (1-9 volume %), glycerin (1-15 volume %), DMA (0.5-3 volume %), PVP (0.5-6 volume %), or Tween 80 (0.08-0.4 volume %).

The pharmaceutical compositions of the present invention may also include stabilisers or antioxidants such as ascorbic acid, gentisic acid or para-aminobenzoic acid.

The compound of the present invention can be an isomer of the formula (Ia), (Ib), (IIa) or (IIb):

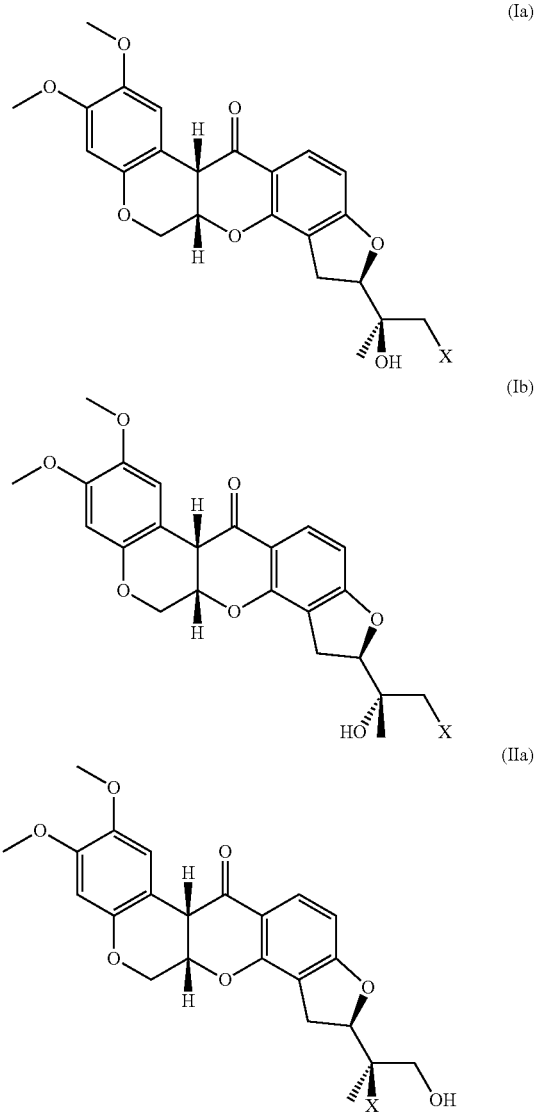

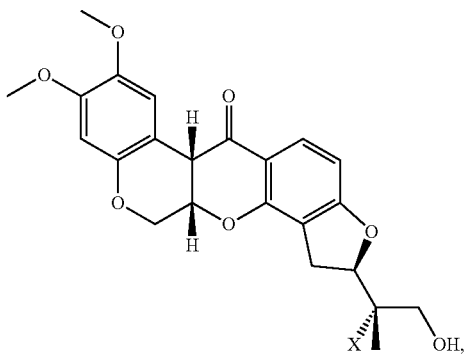

(IIb)

wherein X is a gamma-emitting radionuclide.

Examples of gamma-emitting radioisotopes that may be used in the radiotracers of the present invention include without limitation $^{76}$Br, $^{77}$Br, $^{82}$Br, $^{123}$I, $^{124}$I, $^{125}$I and $^{131}$I.

More specifically, the compound of the present invention may be selected from the group consisting of:

(2R,6aS,12aS)-2-((S)-1-[$^{76}$Br]bromo-2-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-1-[$^{76}$Br]bromo-2-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-1-[$^{77}$Br]bromo-2-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-1-[$^{77}$Br]bromo-2-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-1-[$^{82}$Br]bromo-2-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-1-[$^{82}$Br]bromo-2-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-hydroxy-1-[$^{124}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{124}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-hydroxy-1-[$^{125}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{125}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-hydroxy-1-[$^{131}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{131}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{76}$Br]bromo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-[$^{76}$Br]bromo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{77}$Br]bromo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-[$^{77}$Br]bromo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{82}$Br]bromo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-[$^{82}$Br]bromo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{124}$I]iodo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-[$^{124}$I]iodo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{125}$I]iodo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((S)-2-[$^{125}$I]iodo-1-hydroxypropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{131}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{131}$I]iodo-1-hydroxypropan-2-yl)-8,9-dimethoxy-1,2,12,12a-tetrahydrochromeno[3,4-b]furo[2,3-h]chromen-6(6aH)-one.

In another example, the compound of the present invention is selected from the group consisting of:

(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

The present invention also relates to a composition comprising a mixture of two or more of the compounds of formulas (Ia), (Ib), (IIa) and (IIb).

In particular, the present invention provides a composition comprising a mixture of two or more compounds selected from the group consisting of:

(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

The present application also provides a pharmaceutical composition comprising one or more than one compound selected from the group consisting of:

(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-1-[$^{123}$I]iodopropan-2-yl)-
8,9-dimethoxy-1,2,12,12a-tetrahydrochromeno[3,4-b]
furo[2,3-h]chromen-6(6aH)-one;
(2R,6aS,12aS)-2-((R)-2-[$^{123}$I]iodo-1-hydroxypropan-2-yl)-
8,9-dimethoxy-1,2,12,12a-tetrahydrochromeno[3,4-b]
furo[2,3-h]chromen-6(6aH)-one, and
(2R,6aS,12aS)-2-((S)-2-[$^{123}$I]iodo-1-hydroxypropan-2-yl)-
8,9-dimethoxy-1,2,12,12a-tetrahydrochromeno[3,4-b]
furo[2,3-h]chromen-6(6aH)-one, and
a physiologically acceptable vehicle.

Radio-iodinated derivatives of the present invention can be prepared according to the synthetic schemes illustrated in FIG. 1. In one example, rotenone (1) may be allowed to react with a sodium salt of a radioactive halide in aqueous solution in the presence of the oxidant Iodogen™ (1,3,4,6-tetrachloro-3α,6α-diphenyl glycoluril; Pierce (Rockford, Ill.)) to form radioactive isomeric alkyl halides (Ia), (Ib), (IIa) and (IIb). Alternatively, rotenone (1) may be allowed to react with a sodium salt of a non-radioactive halide in aqueous solution in the presence of Iodogen™ to form non-radioactive isomeric alkyl halides (IIIa), (IIIb), (IVa) and (IVb), which can be converted to isomers (Ia), (Ib), (IIa) and (IIb) using an isotope exchange reaction. Isomers (Ia), (Ib), (IIa) and (IIb) can be used together or separated from each other and used individually as radiotracers in SPECT imaging according to the present invention.

The amount of the compound of formula (I) and/or the compound of formula (II) included in the pharmaceutical composition of the present invention should be sufficient to provide satisfactory imaging. For example, the dosage can be from about 1.0 to about 50 millicuries or any subrange or value therebetween, from about 1.0 to about 10 millicuries or any subrange or value therebetween, from about 10 to about 20 millicuries or any subrange or value therebetween, from about 20 to about 30 millicuries or any subrange or value therebetween, from about 30 to about 40 millicuries or any subrange or value therebetween, or from about 40 to about 50 millicuries or any subrange or value therebetween. The amount and activity of each one of the radiotracers of the present invention should be selected such that it remains in the patient for a period of about 1 to 3 hours, although both longer and shorter time periods are acceptable.

The present invention also relates to a method of imaging a region in a patient, comprising:
administering to the patient a diagnostically effective amount of a composition comprising a compound of formula (I), a compound of formula (II) or a mixture thereof:

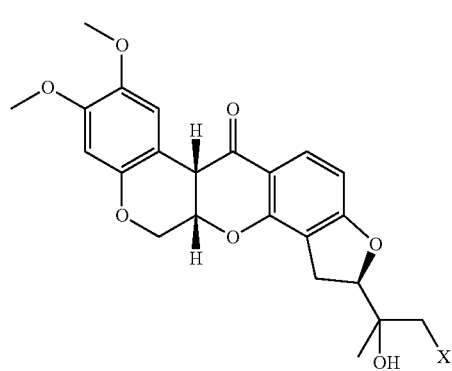

(I)

-continued

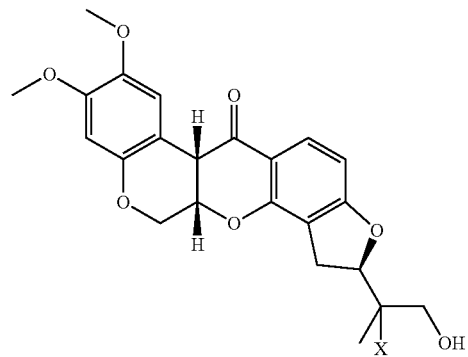

(II)

wherein X is a gamma-emitting radionuclide, and a physiologically acceptable vehicle, a portion of the composition being retained in the region of the patient, detecting radiation in the region of the patient, and obtaining an image of the region of the patient.

In one example of the above-defined method, the compound administered to the patient is an isomer of the formula (Ia), (Ib), (IIa), (IIb) or a mixture thereof,

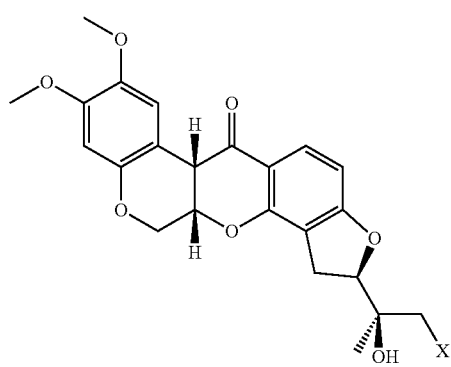

(Ia)

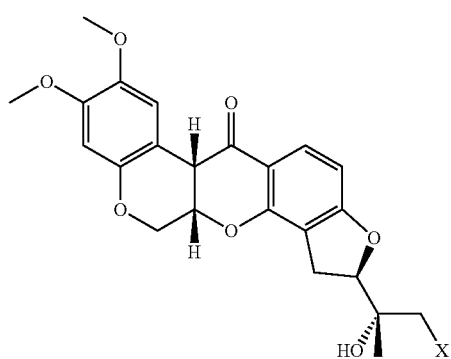

(Ib)

-continued

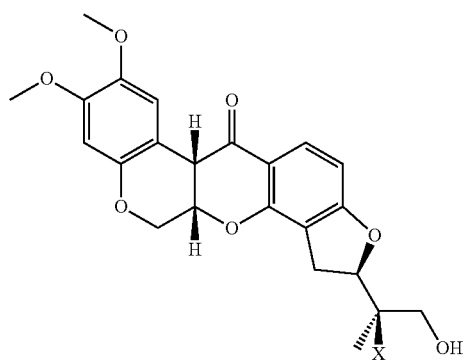

(IIa)

(IIb)

wherein X is a gamma-emitting radionuclide.

In a further example of the above-defined method, the compound administered to the patient is one or more than one compound selected from the group consisting of:

(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and (2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

In another example of the above defined method, the region of the patient is the heart.

In a further example of the method described above, the region of the patient being imaged is the heart, and prior to the step of administering, stress is induced in the patient for a period of about 1 to about 8 minutes by having the patient exercise or by administering a stress agent to the patient, such as dipyridamole, dobutamine, adenosine, or regadenosan.

In another example of the method defined above, the compound of formula (I) and/or the compound of formula (II) is administered to the patient 30 seconds to 1 minute after the period in which stress has been induced in the patient.

The following examples are included to demonstrate particular embodiments of the invention. Those of skill in the art should, in light of the present disclosure, appreciate that many changes can be made in the specific embodiments which are disclosed and still obtain a like or similar result without departing from the spirit and scope of the invention.

Labelling of Rotenone:

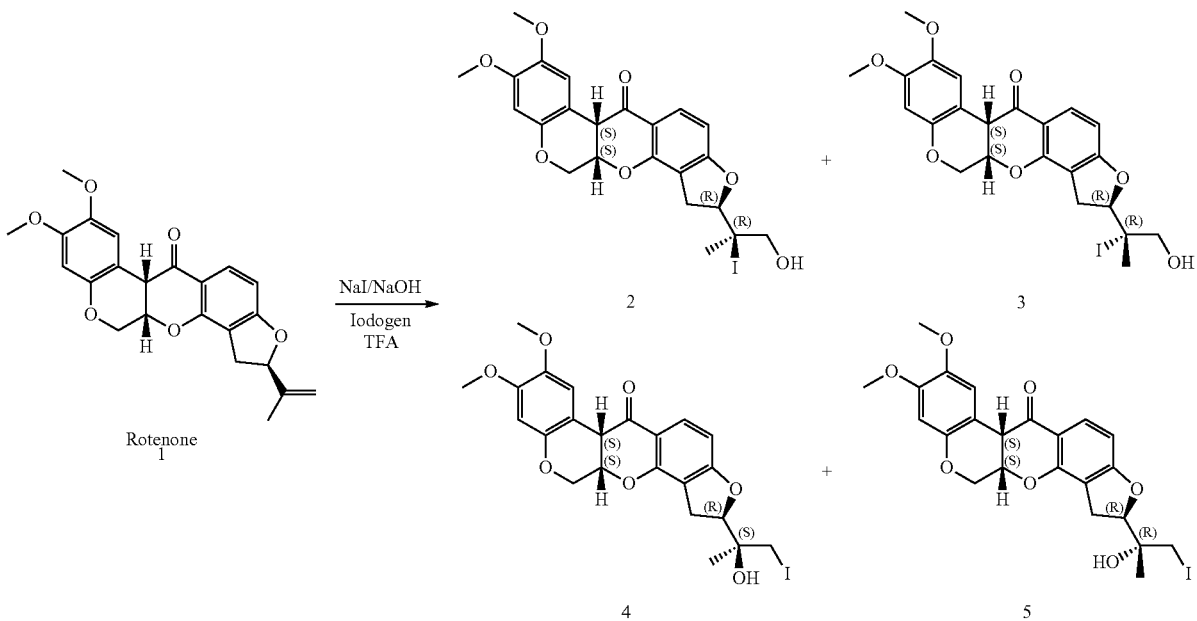

Rotenone (1, 42.5 mg) in TFA (17 mL) was mixed with NaI (81 mg) in NaOH solution (0.1 M, 5 mL). To the stirred mixture was added Iodogen™ (45 mg) in TFA (3 mL) at room temperature. The reaction mixture was stirred at 60° C. for 45 min and concentrated under reduced pressure. Water (20 mL) was poured in and extracted with $CH_2Cl_2$ (20 mL×3), dried over anhydrous $Na_2SO_4$, filtered, and concentrated under reduced pressure to yield a green oil. This residue was taken up by $CH_2Cl_2$ (1 mL) and subjected to HPLC purification. The column used was a preparative Luna 5u C18(2) of 21.2× 250 mm and 5 μm (Phenomenex, Calif.). The sample was eluted at a flow rate of 6 mL min$^{-1}$, using a combination of water and EtOH (50/50). The detector was set to 290 nm. The desired product (retention time 51-63 min) was collected and evaporated to dryness to yield a mixture of isomers 2-5 as a white solid (3 mg, 5.6%). The diastereomeric pair 2 and 3 and the diastereomeric pair 4 and 5 were produced in the following ratio: 13% 2 and 3: 87% 4 and 5.

Figure 2:
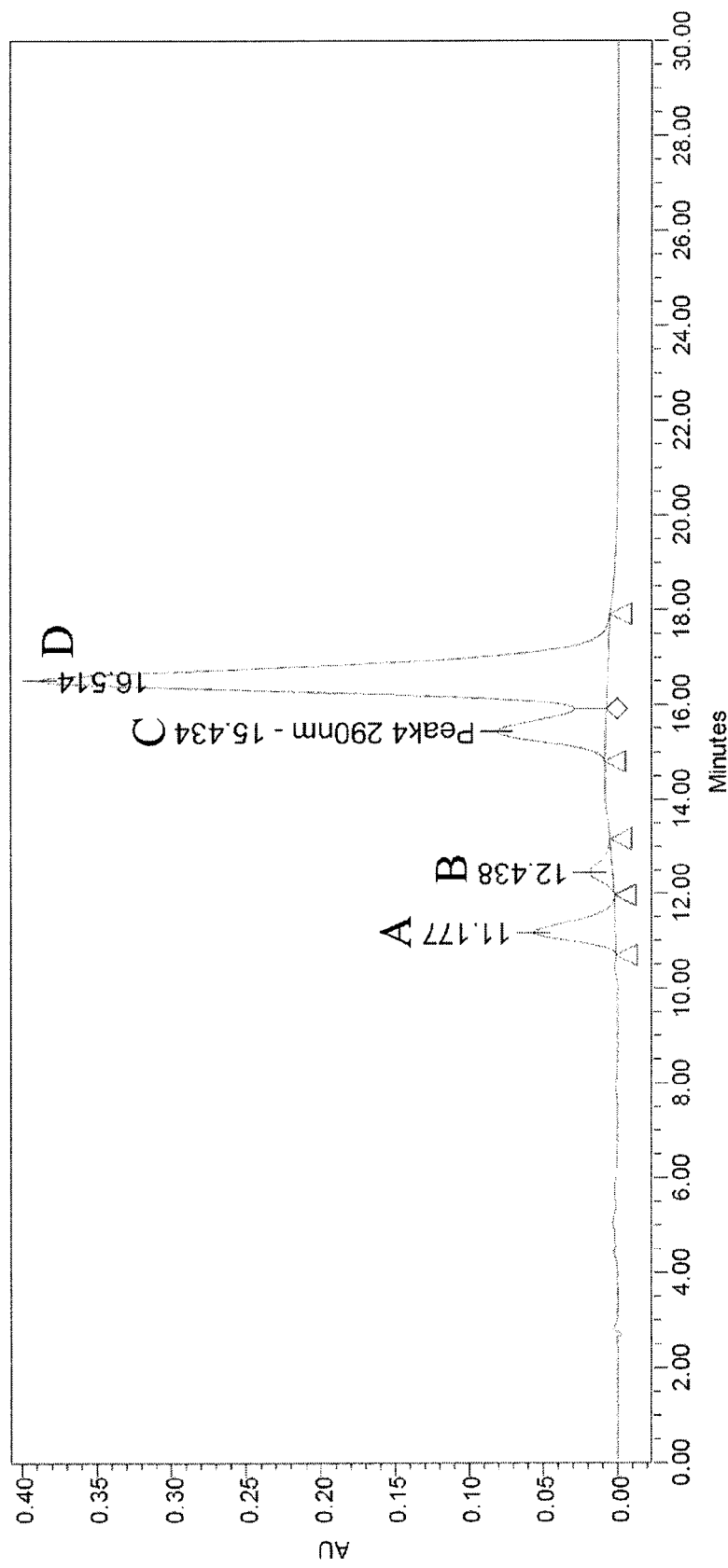
FIG. 2 shows a chromatogram of non-radioactive [$^{127}$I] iodinated rotenone derivatives of the present invention.

FIG. 2 shows a UV chromatogram of a purified mixture of iodinated rotenone where peaks A and B represent diastereomeric pair 2 and 3 and peaks C and D represent diastereomeric pair 4 and 5. The absolute configuration at the 6' position of each isomer corresponding to peaks A-D was not determined.

The isomers corresponding to peaks A-D were purified and analysed by $^1$H- and $^{13}$C-NMR and HRMS.

Peak A: $^1$H NMR (300 MHz, CDCl3) δ 7.83 (d, J=8.6 Hz, 1H), 6.74 (s, 1H), 6.49 (d, J=8.6 Hz, 1H), 6.43 (s, 1H), 5.02-4.89 (m, 1H), 4.62 (dd, J=12.1, 3.1 Hz, 1H), 4.28-4.10 (m, 2H), 3.92 (d, J=11.8 Hz, 1H), 3.84 (d, J=4.0 Hz, 2H), 3.79 (s, 3H), 3.74 (s, 3H), 3.31 (dd, J=14.3, 7.9 Hz, 1H), 3.13 (dd, J=15.9, 8.2 Hz, 1H), 1.91 (s, 3H). $^{13}$C NMR (75 MHz, CDCl$_3$) δ 188.97, 166.40, 157.79, 149.46, 147.38, 143.85, 130.15, 113.65, 112.54, 110.15, 104.89, 104.66, 100.89, 88.44, 72.24, 71.29, 66.28, 59.80, 56.32, 55.89, 44.61, 32.56, 26.61. HRMS for $C_{23}H_{23}IO_7$ EI calcd. 538.0488. Found 538.0514.

Peak B: $^1$H NMR (500 MHz, CDCl3) δ 7.82 (d, J=7.7 Hz, 1H), 6.74 (s, 1H), 6.53 (s, 1H), 6.46 (d, 1H), 5.09 (t, J=8.7 Hz, 1H), 4.96 (s, 1H), 4.70-4.55 (m, 1H), 4.19 (d, J=12.1 Hz, 1H), 3.88-3.67 (m, 9H), 3.53-3.34 (m, 1H), 3.29-3.10 (m, 1H), 1.93 (s, 3H). $^{13}$C NMR (126 MHz, CDCl3) δ 188.91, 166.87, 157.71, 149.49, 147.36, 143.84, 130.04, 113.60, 112.26, 110.20, 104.72, 104.55, 100.90, 88.09, 72.25, 71.43, 66.17, 58.68, 56.29, 55.83, 44.58, 31.65, 23.52. HRMS for $C_{23}H_{23}IO_7$ EI calcd. 538.0488. Found 538.0473.

Peak C: HRMS for $C_{23}H_{23}IO_7$ EI calcd. 538.0488. Found: 538.0550.

Peak D: $^1$H NMR (500 MHz, CDCl$_3$) δ 7.81 (d, J=8.6 Hz, 1H), 6.73 (s, 1H), 6.46 (d, J=8.6 Hz, 1H), 6.43 (s, 1H), 4.94-4.88 (m, 2H), 4.60 (dd, J=12.1, 3.1 Hz, 1H), 4.17 (d, J=12.1 Hz, 1H), 3.83 (d, J=4.0 Hz, 1H), 3.79 (s, 3H), 3.74 (s, 3H), 3.46 (d, J=10.5 Hz, 1H), 3.36 (d, J=10.5 Hz, 1H), 3.20 (dd, J=16.2, 9.8 Hz, 1H), 3.12 (dd, J=16.2, 7.9 Hz, 1H), 1.98 (bs, 1H), 1.36 (s, 3H); $^{13}$C NMR (126 MHz, CDCl$_3$) δ 188.96, 166.76, 157.89, 149.49, 147.36, 143.85, 129.99, 113.60, 113.10, 110.21, 104.81, 104.59, 100.89, 87.69, 72.25, 71.71, 66.22, 56.30, 55.85, 44.58, 27.35, 22.19, 17.46; HRMS for $C_{23}H_{23}IO_7$ EI calcd. 538.0488. Found 538.0590. The structure of the isomer corresponding to peak D was confirmed using HMQC, HMBC and COSY NMR experiments.

Radiolabelling of Rotenone:

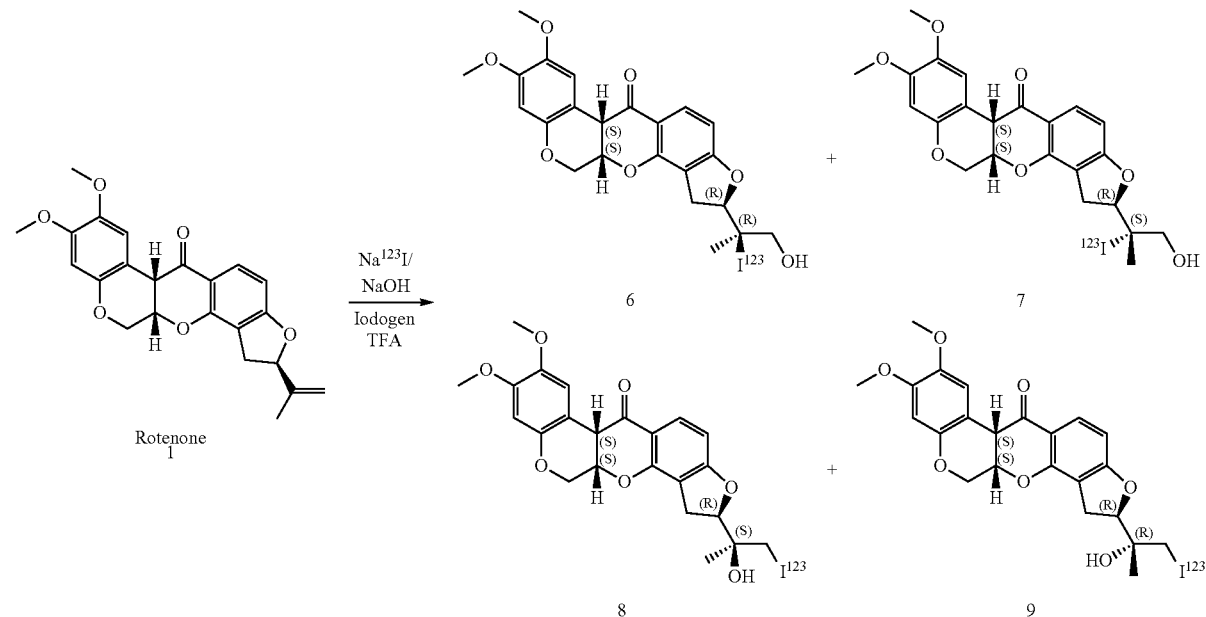

12.5 mCi of a Na$^{123}$I solution in 0.1 M NaOH was added into a 1.5 mL BioRad vial. The volume of Na$^{123}$I solution was calculated based on the activity concentration on a corresponding technical datasheet. 170 μL of a solution of rotenone (1, 2.5 mg/mL) in trifluoroacetic acid (TFA) and 30 μL of an Iodogen™ solution (0.75 mg/mL) in TFA were added. The ratio of rotenone (1) to Iodogen™ was 20:1. The mixture was heated on a thermomixer at 60° C., 600 rpm for 45 min. After cooling at room temperature for 5 min, the reaction mixture was applied to an HPLC column (Phenomenex Luna C18(2), 5 μm, 100 Å, 250×4.6 mm column and 50% ethanol/50% water as a mobile phase; Flow rate: 1.0 mL/min) to purify the crude reaction mixture. Radiometric detection was conducted using an open window going from 0-2048 keV (the I-123 peak was detected at 159 keV). A purified solution containing isomers 6-9 was isolated and heated at 60° C. under a constant supply of nitrogen to partially evaporate ethanol. A charcoal filter was used as a vent and also to absorb any free I-123 during the concentration process. The radiochemical purity of the isolated isomers was ≥90%. The overall yield of isomers 6-9 after HPLC purification was 30%. The diastereomeric pair 6 and 7, and the diastereomeric pair 8 and 9 were produced in the following ratios: 12% 6 and 7: 88% 8 and 9.

Figure 3A:
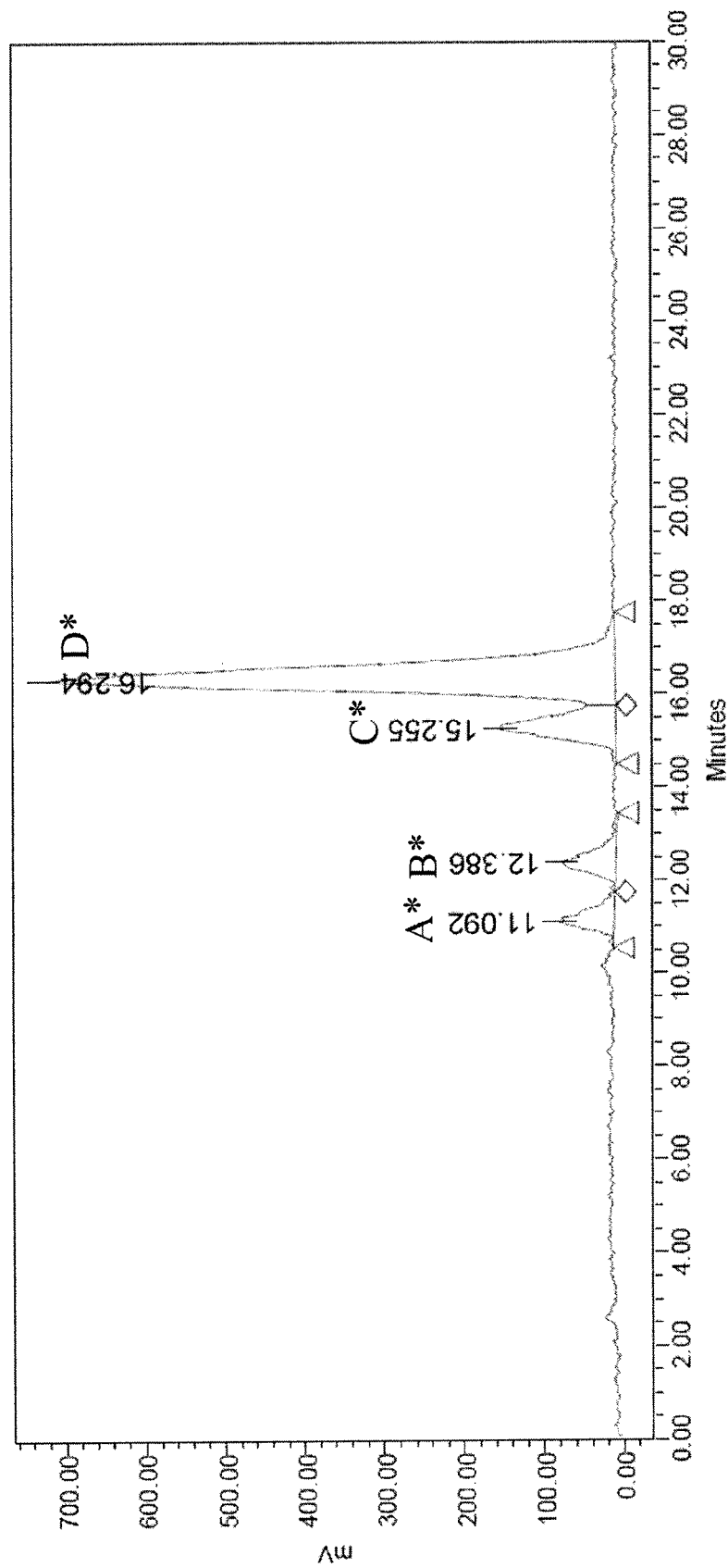
FIG. 3A shows a chromatogram of a mixture of [$^{123}$I] iodinated rotenone derivatives of the present invention.
Figure 3B:
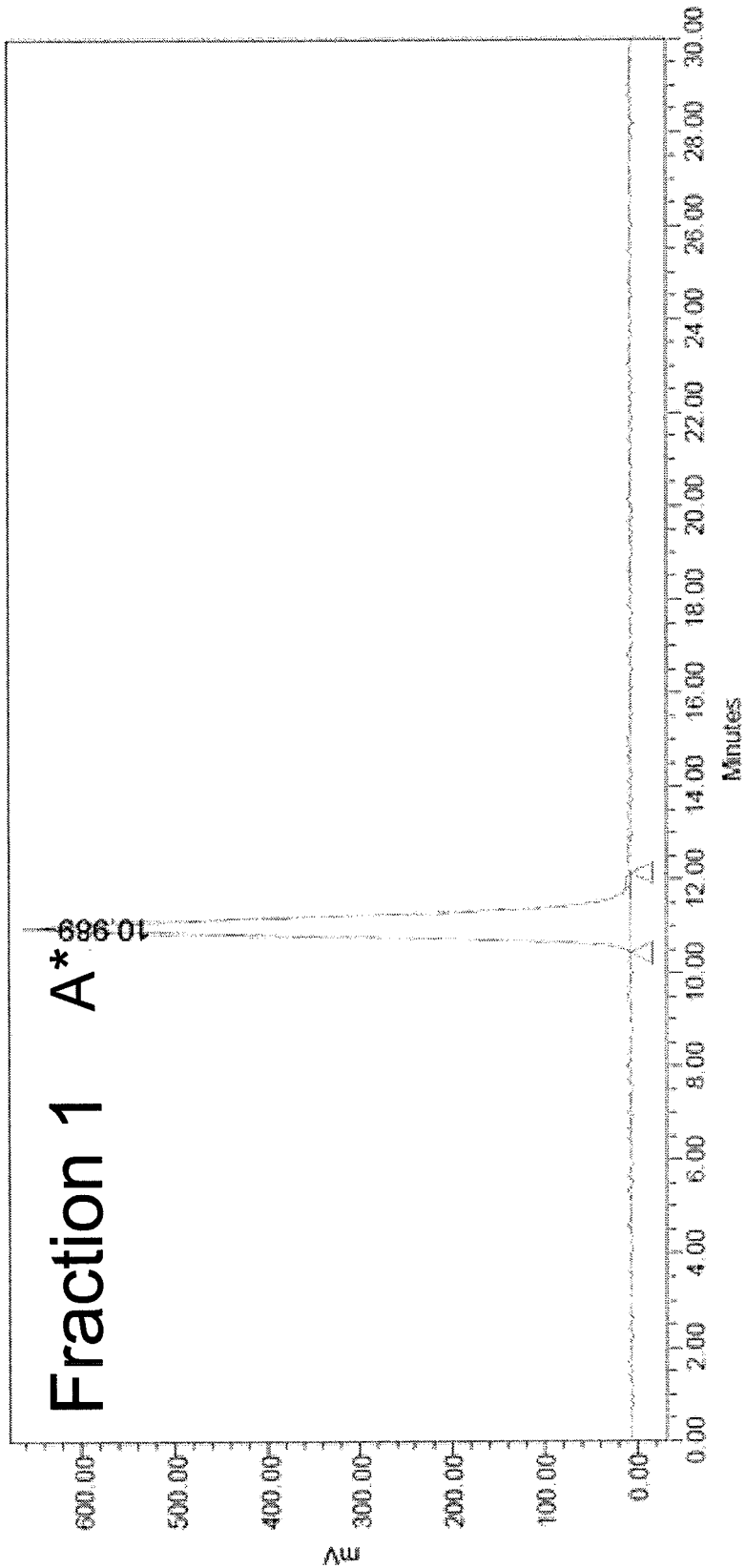
FIGS. 3B-3E show chromatograms of purified fractions of the mixture of [$^{123}$I] iodinated rotenone derivatives of FIG. 3A.
Figure 3C:
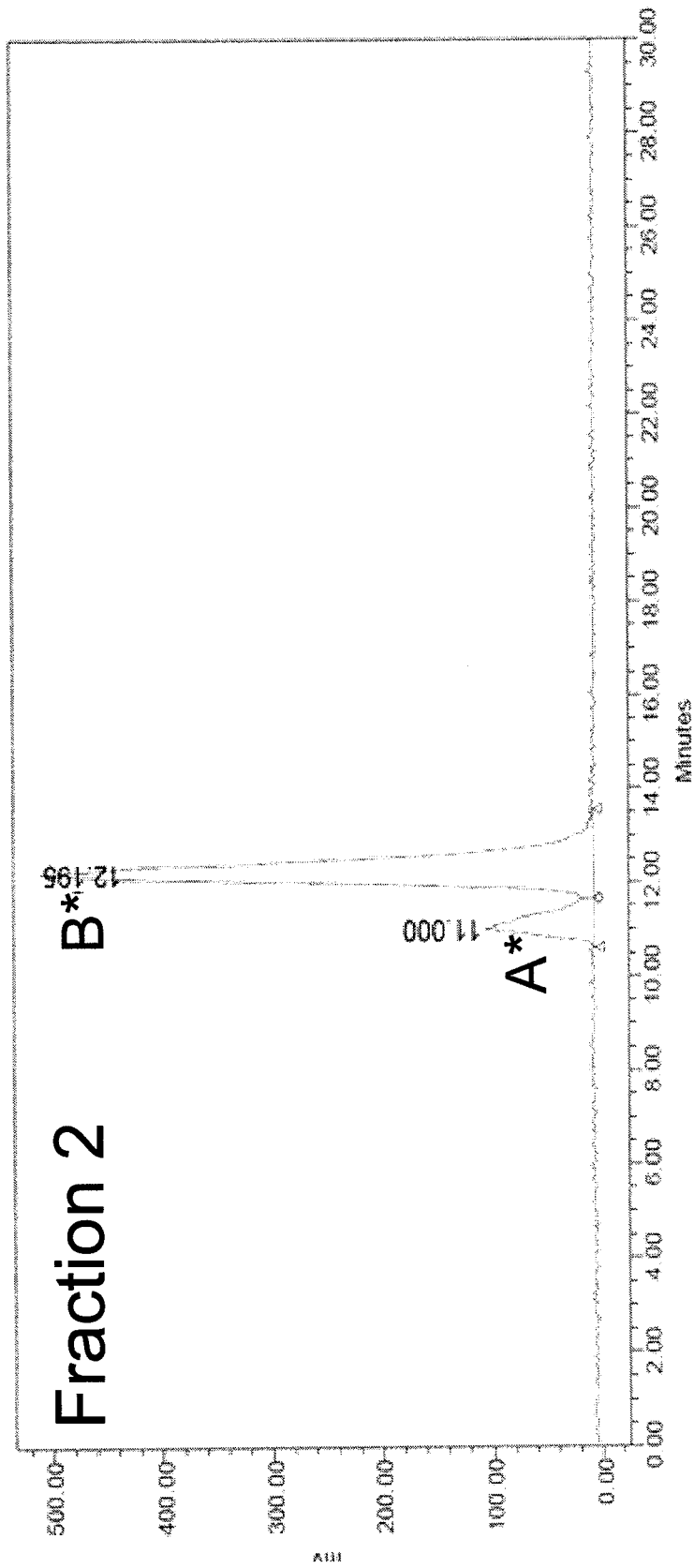
Figure 3D:
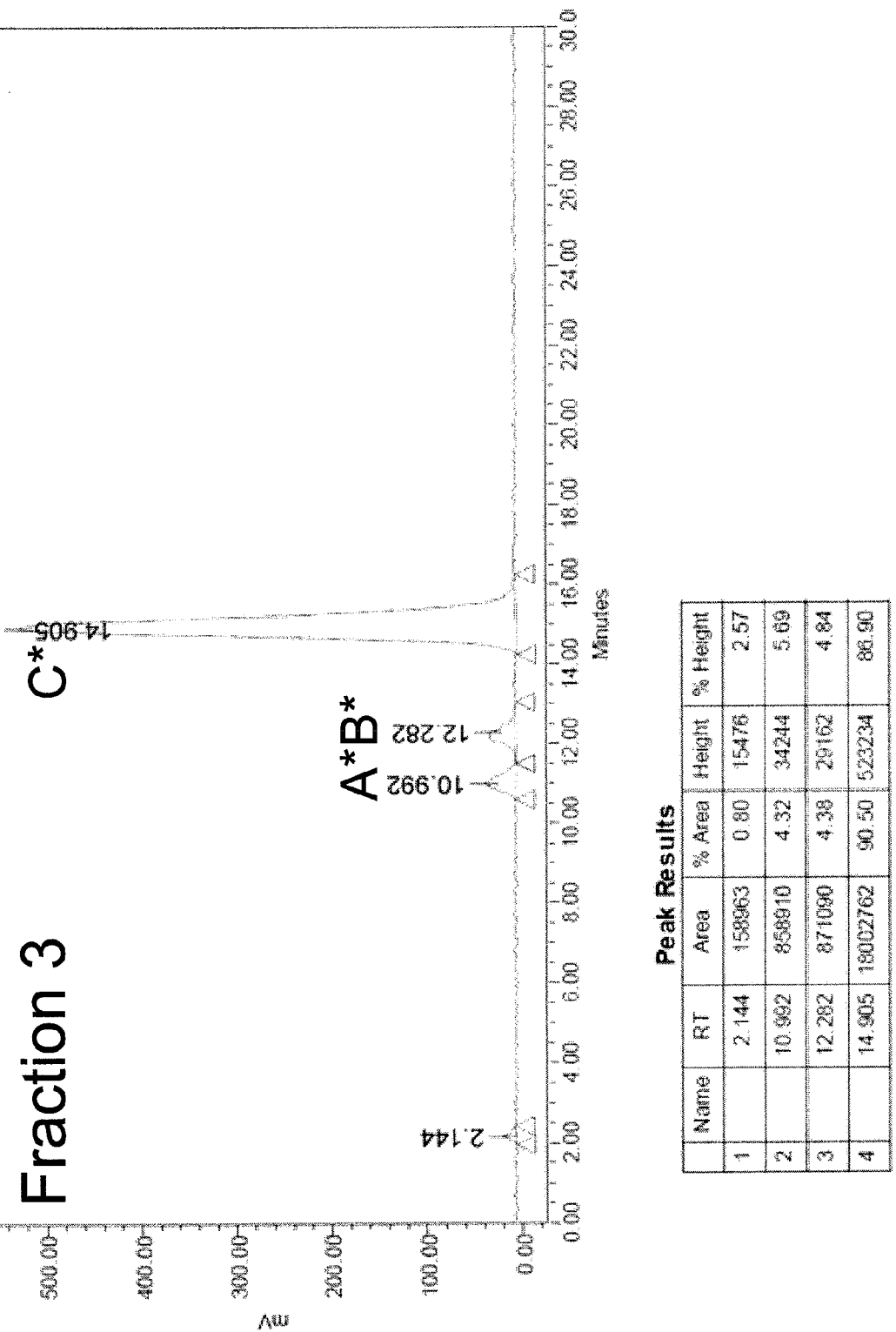
Figure 3E:
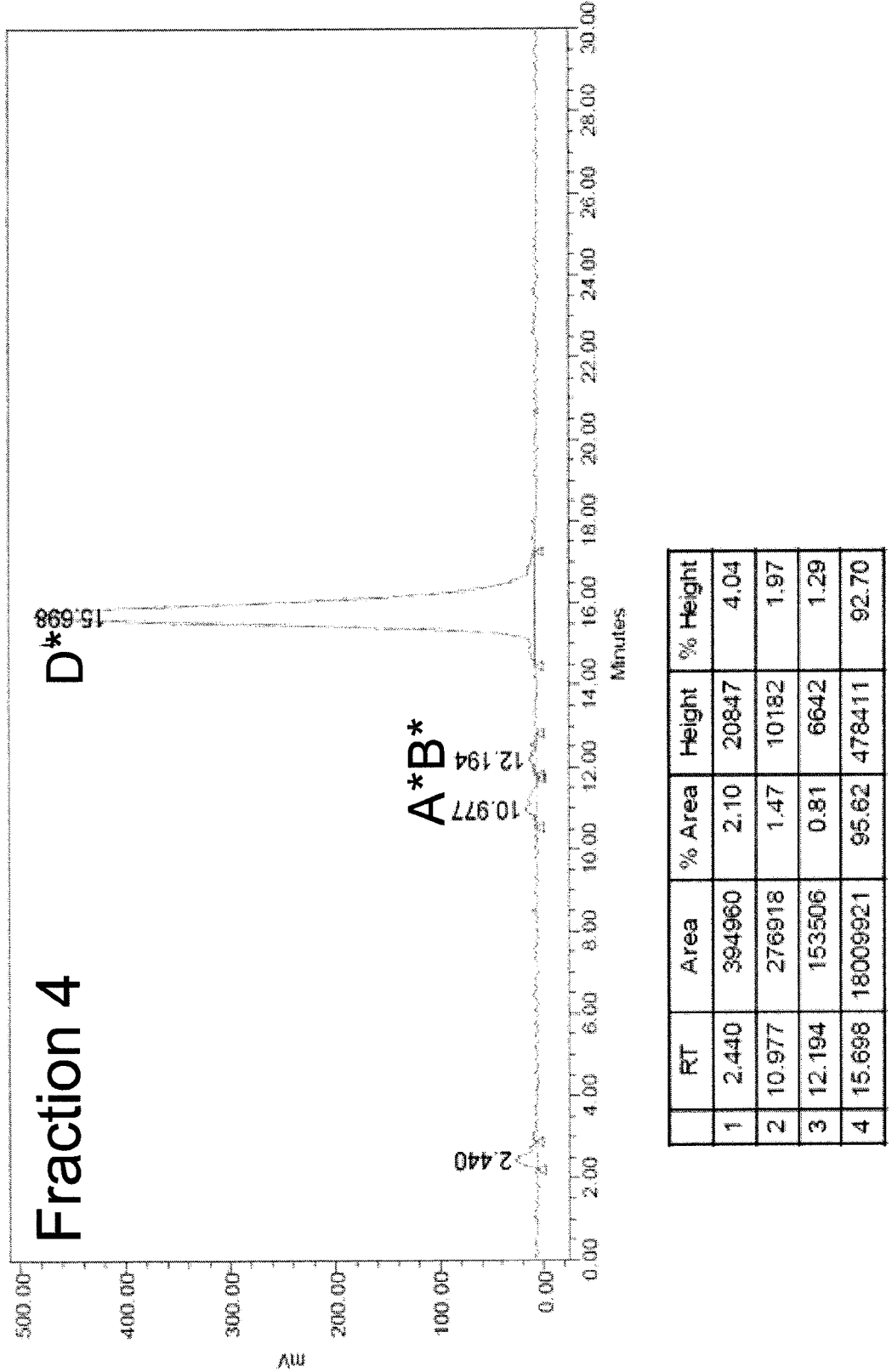

FIG. 3A shows a chromatogram of a purified reaction mixture with peaks A* and B* representing diastereomeric pair 6 and 7 and peaks C* and D* representing diastereomeric pair 8 and 9, based upon a comparison of the elution times of these peaks with those of the peaks A and B (corresponding to non-radioactive diastereomeric pair 2 and 3) and peaks C and D (corresponding to non-radioactive diastereomeric pair 4 and 5) shown in FIG. 2. The absolute configuration at the 6' position of each isomer corresponding to peaks A*-D* was not determined. FIGS. 3B-3E show chromatograms of purified fractions of the purified reaction mixture containing isomers 6-9.

Cell Uptake Assays with Labeled Rotenone Derivatives

Figure 4:
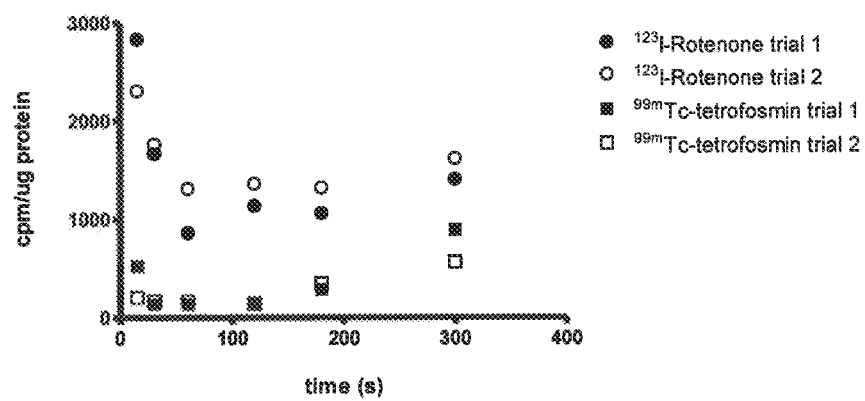
FIG. 4 shows the amount of internalization of the [$^{123}$I] iodinated rotenone derivatives of the present invention and $^{99m}$Tc-tetrofosmin in cultured cardiomyocytes. Primary neonatal cardiomyocytes were incubated with [$^{123}$I]iodinated rotenone derivatives of the present invention (rot) or $^{99m}$Tc-tetrofosmin (myo). The amount of internalization is shown as cpm/total ug protein. The results of two separate trials for each compound are shown.

An internalization assay was used to test the in vitro function of candidate perfusion tracers. In this assay, cultures of rat cardiomyocytes were plated at a density of $3-5\times10^5$ cells/mL into 24-well tissue culture plates. The cardiomyocytes were then incubated with 0.5 μCi of radiolabeled tracer $^{99m}$Tc-tetrofosmin (Myoview™) or [$^{123}$I] iodinated rotenone (mixture containing isomers 6-9) mixed in cell culture medium (DMEM) and incubated for up to five minutes. At different time points, the total supernatant was collected, the cells were washed twice with PBS and then exposed and lysed with 1 M NaOH for 15 min. Samples were counted in a gamma well counter and the cellular protein was determined for the lysed samples. The data was analyzed to represent the total "internalized" fraction expressed as cpm per total protein (FIG. 4).

From preliminary assays, cellular internalization of $^{123}$I-Rotenone was rapid and immediate with maximal uptake by 15 s. In comparison, $^{99m}$Tc-tetrofosmin internalization was evident at 15 s but a gradual increase was seen up to 5 min. Internalization of [$^{123}$I] iodinated rotenone was not as high at subsequent time points compared to 15 seconds. Relative to $^{99m}$Tc-tetrofosmin, [$^{123}$I] iodinated rotenone remained higher at all time points suggesting that [$^{123}$I] iodinated rotenone may have a higher capacity for cardiomyocytes perfusion than $^{99m}$Tc-tetrofosmin in vitro.

Stability of Compounds 6-9

Rotenone was radiolabelled with $^{123}$I according to the method described above to produce a mixture of compounds 6-9. 0.56 mL of a 15.5 mCi/mL mixture of compounds 6-9 in 23% ethanol was diluted with 3.84 mL of 10 mM sodium acetate, pH 6.5 and 0.10 mL of 95% ethanol, to produce 4.5 mL of a 1.9 mCi/mL solution having a value of pH of about 5. The solution was left undisturbed for 22 hours at room temperature. Analysis of the mixture of compounds after 22 hours revealed that there was no substantial hydrolytic degradation of these products.

Ex Vivo Biodistribution of a Mixture Containing Isomers 6-9 (12% 6 and 7 Diastereomers; 88% 8 and 9 Diastereomers) in Sprague-Dawley Rats An amount of 0.5 mL of a 2.4 mCi/mL mixture of compounds 6-9 (Mixture A: composition comprising isomeric mixture of 12% 6 and 7 diastereomers; 88% 8 and 9 diastereomers) in 7% ethanol was diluted with 0.58 mL of 10 mM sodium acetate, pH 6.5 and 0.023 mL of 95% ethanol, to produce a 1.1 mL of a 1.1 mCi/mL solution having a value of pH of about 5. An amount of 0.8 mL of this solution (0.9 mCi) was injected through the tail veins of 14 Sprague-Dawley rats. Six of the rats were used to assess biodistribution of the mixture of compounds 6-9 after two hours, and the remaining eight rats were used to determine the biodistribution of the compounds after 24 hours. Selected organs were collected and weighed and the activity was measured for each organ with a gamma well counter using the detection range of 138-207 keV, and the measured values of activity were decay-corrected to the time of injection. The values of percentage of injected dose per gram of tissue (% ID/g) were calculated by taking the ratio of the activity in the organ over the total activity injected per gram of tissue. Uptake in the heart of the rat was confirmed by the SPECT/CT images shown in FIG. 5, in which the heart is well defined.

Figure 5:
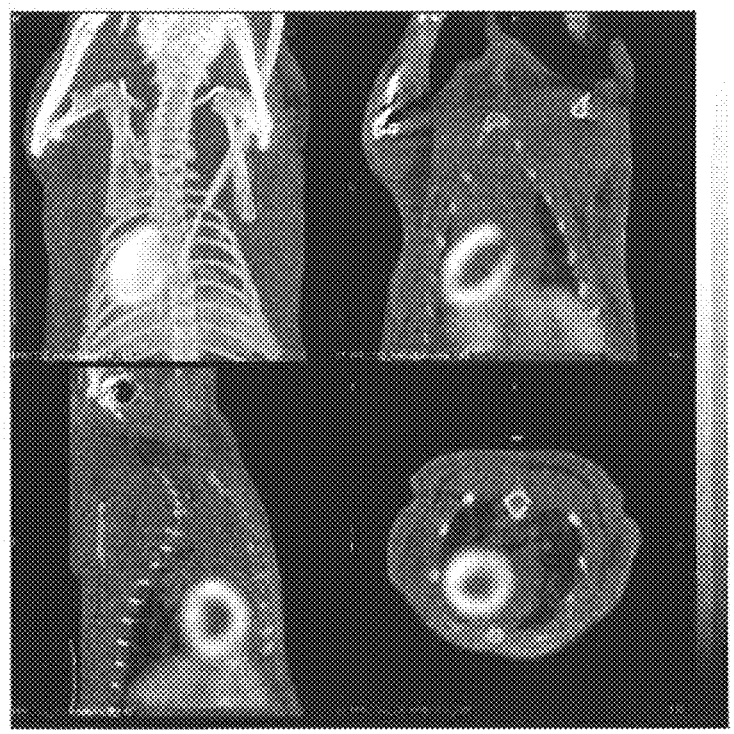
FIG. 5 shows SPECT images of $^{123}$I-Rotenone distribution at 30 minutes (summed images) following injection in a rat. Starting from the top left and proceeding clockwise are shown the maximum intensity projection, the coronal view, the transverse view and the sagittal view.

As shown in Table 1, at 2 hours post injection, there was a significant uptake in the myocardial tissue (2.01±0.48%), while the tracer accumulations in all other organs were lower than heart, except stomach (3.26±1.77%). The heart to blood ratio was high (8.37±3.97) at 2 hr p.i., indicating the tracer was rapidly extracted from the blood to myocardium. The ratios of heart uptake to surrounding organs were also high (heart/liver: 2.98±0.93; heart/lung: 4.11±1.04), which is consistent with the minimal interference from the background in the SPECT/CT images (FIG. 5).

After 24 hr, the majority of the mixture of compounds 6-9 (82-98%) had been cleared from most organs, the washout rate from stomach (35%) and urine/bladder (16%) is lower. The high urine uptake at 24 hr p.i. is expected, due to the common renal excretion route for radiopharmaceuticals based on small molecules. Accumulation in the stomach and slow clearance is likely related to the activity of the sodium iodide symporter (NIS). NIS is a transmembrane glycoprotein that exchanges sodium and iodide ions and is expressed at high levels in the intestinal lumen in mammals. The clearance from heart was faster than liver, blood and lung, as shown from the significantly reduced heart to blood, heart to liver and heart to lung ratios from 2 hr to 24 hr p.i.

The amount of thyroid uptake is the indication to the degree of in vivo deiodination. The thyroid uptake of the mixture of compounds 6-9 was low at 2 hr p.i. (0.33±0.12% ID/organ), indicating the tracer is relatively stable within 2 hrs. Thyroid uptake was significantly increased at 24 hr p.i., with the calculated linear thyroid accumulation rate about 0.13% per hour from 2 hr to 24 hr, which is consistent with the deiodination of the tracer at 24 hr p.i. In the current study, a thyroid blocking reagent was not employed as it was necessary to understand the normal "unaffected" distribution of the mixture of compounds 6-9.

TABLE 1

Biodistribution of a mixture containing isomers 6-9 (12% 6 and 7 diastereomers; 88% 8 and 9 diastereomers) in Sprague-Dawley rats % ID/g

| Tissue | Mixture containing 5.6% A*, 6.4% B*, 14.0% C*, 74.0% D* (12% 6 and 7 and 88% 8 and 9) | |
|---|---|---|
| | 2 hr p.i. (n = 6) | 24 hr p.i. (n = 8) |
| Urine/Bladder | 0.918 ± 0.660 | 0.768 ± 0.656 |
| Liver | 0.709 ± 0.210 | 0.042 ± 0.011 |
| Femur | 0.242 ± 0.049 | 0.025 ± 0.005 |

TABLE 1-continued

Biodistribution of a mixture containing isomers 6-9 (12% 6 and 7 diastereomers; 88% 8 and 9 diastereomers) in Sprague-Dawley rats % ID/g

| | Mixture containing 5.6% A*, 6.4% B*, 14.0% C*, 74.0% D* (12% 6 and 7 and 88% 8 and 9) | |
|---|---|---|
| Tissue | 2 hr p.i. (n = 6) | 24 hr p.i. (n = 8) |
| Muscle | 0.357 ± 0.033 | 0.024 ± 0.008 |
| Spleen | 0.234 ± 0.026 | 0.032 ± 0.010 |
| Blood | 0.257 ± 0.046 | 0.060 ± 0.023 |
| Brain | 0.098 ± 0.041 | 0.003 ± 0.001 |
| Intestine | 0.846 ± 0.065 | 0.122 ± 0.066 |
| Kidney | 0.700 ± 0.201 | 0.044 ± 0.010 |
| Heart | 2.010 ± 0.477 | 0.045 ± 0.014 |
| Lung | 0.502 ± 0.104 | 0.055 ± 0.019 |
| Testis/overies | 0.220 ± 0.055 | 0.040 ± 0.012 |
| Stomach | 3.263 ± 1.773 | 2.121 ± 0.378 |
| Thyroid | 1.368 ± 0.458 | 13.329 ± 6.225 |
| Thyroid (% ID/organ) | 0.334 ± 0.122 | 3.160 ± 0.948 |
| Heart/Liver | 2.98 ± 0.93 | 1.08 ± 0.19 |
| Heart/Blood | 8.37 ± 3.97 | 0.79 ± 0.19 |
| Heart/Lung | 4.11 ± 1.04 | 0.85 ± 0.13 |

Ex Vivo Biodistribution of Purified Fractions of a Mixture of Isomers 6-9 in Sprague-Dawley Rats A biodistribution study was conducted according to the method described above using purified fractions of the mixture of isomers 6-9 (Mixture A).

FIGS. 3B-3E show HPLC chromatograms of the four separate fractions used in the biodistribution study: Fraction 1: fraction comprising 100% of Component A*; Fraction 2: fraction comprising an isomeric mixture comprising 15.2% Component A* and 84.8% Component B*; Fraction 3: fraction comprising an isomeric mixture comprising 4.4% Component A*, 4.4% Component B* and 91.2% Component C*; Fraction 4: fraction comprising an isomeric mixture comprising 1.5% Component A*, 0.8% Component B* and 97.7% Component D*.

Table 2 shows biodistribution data (% ID/g tissue at 2 hr. p.i.) for each of the Fractions 1-4. The data suggests that the biodistribution for each of the isomers 6-9 is similar in most organs, except for the isomer represented by peak B*, which shows slightly lower heart uptake and much lower liver uptake, resulting in a relatively higher heart to liver ratio. The intestine uptake of B* is also significantly higher than others.

As a result of the similarity in biodistribution of the four isomers 6-9, it is believed that a mixture containing various ratios of these four isomers can be used without further purification in SPECT imaging.

TABLE 2

Biodistribution of purified compounds 6-9 in Sprague-Dawley rats at 2 hr p.i. % ID/g, 2 hr p.i.

| Tissue | Fraction 1 (100% A*) (n = 3) | Fraction 2 (15.2% A*, 84.8% B*) (n = 5) | Fraction 3 (4.4% A*, 4.4% B*, 91.2% C*) (n = 6) | Fraction 4 (1.5% A*, 0.8% B*, 97.7% D*) (n = 6) |
|---|---|---|---|---|
| Urine | 0.528 ± 0.134 | 1.083 ± 0.861 | 1.221 ± 0.717 | 0.910 ± 0.806 |
| Liver | 1.363 ± 0.101 | 0.189 ± 0.058 | 0.981 ± 0.251 | 0.840 ± 1.189 |
| Femur | 0.239 ± 0.083 | 0.174 ± 0.048 | 0.251 ± 0.031 | 0.248 ± 0.047 |
| Muscle | 0.369 ± 0.117 | 0.300 ± 0.118 | 0.372 ± 0.129 | 0.324 ± 0.040 |
| Spleen | 0.177 ± 0.031 | 0.121 ± 0.034 | 0.242 ± 0.044 | 0.271 ± 0.020 |
| Blood | 0.191 ± 0.040 | 0.169 ± 0.063 | 0.340 ± 0.079 | 0.356 ± 0.145 |
| Brain | 0.063 ± 0.013 | 0.057 ± 0.012 | 0.073 ± 0.025 | 0.123 ± 0.011 |
| Intestine | 0.787 ± 0.186 | 2.062 ± 0.480 | 0.684 ± 0.036 | 0.642 ± 0.148 |
| Kidney | 0.634 ± 0.099 | 0.381 ± 0.069 | 0.671 ± 0.131 | 0.913 ± 0.113 |
| Heart | 1.617 ± 0.335 | 0.841 ± 0.201 | 1.298 ± 0.234 | 2.194 ± 0.365 |
| Lung | 0.357 ± 0.059 | 0.389 ± 0.156 | 0.673 ± 0.449 | 0.511 ± 0.169 |
| Stomach | 1.628 ± 0.837 | 1.910 ± 1.094 | 2.119 ± 0.403 | 1.992 ± 0.955 |
| Thyroid | 0.826 ± 0.191 | 0.943 ± 0.606 | 1.176 ± 0.268 | 1.406 ± 0.320 |
| Testis | 0.128 ± 0.017 | 0.107 ± 0.025 | 0.158 ± 0.015 | 0.181 ± 0.011 |
| Heart/Liver | 1.20 ± 0.35 | 4.64 ± 1.31 | 1.37 ± 0.32 | 2.67 ± 0.56 |
| Heart/Blood | 8.46 ± 0.51 | 5.30 ± 1.44 | 3.93 ± 0.92 | 6.83 ± 2.39 |
| Heart/lung | 4.54 ± 0.59 | 2.38 ± 0.76 | 2.42 ± 0.98 | 4.62 ± 1.44 |

In the following example, the distribution of a mixture of compounds 6-9 (12% 6 and 7; 88% 8 and 9; see FIG. 3A) and microspheres marked with non-radioactive stable isotopes of gold and samarium (BioPal STERIspheres™) were assessed in both the resting and stressed states of a pig heart model.

Following injection, the marked microspheres become lodged by the circulating blood within the blood vessels of the myocardium of the pig. The relative amounts of these stable isotope-marked microspheres residing within the blood vessels of myocardial tissue can be measured in situ by first subjecting the tissue being analysed to neutron activation and then measuring the amount of gamma radiation emitted from the resulting radioactive isotopes contained within the microspheres. The measured amount of gamma radiation emitted by the microspheres is indicative of the former flow of blood containing the microspheres to the tissue in which the microspheres are disposed. The use of stable labelled microspheres in measuring perfusion is described in Reinhardt et al. *Am J. Physiol Heart Circ Physiol* 280: H108-H116, 2001, the disclosure of which is incorporated by reference herein.

Surgical Information

A pig was anesthetized by an intramuscular injection of Telazol. Glycopyrrolate was also administered to facilitate intubation. The pig was intubated and maintained under anesthesia using an isofluorane mask. The pig was then placed in a right lateral position and subjected to a thoracotomy at approximately the third left intercostal space. After opening the left thoracic cavity, the pericardium was incised along the longitudinal axis of the heart and a catheter (Catheter 1) was inserted into the left atrium.

A vascular loop was placed around the left anterior descending (LAD) coronary artery 3 mm below the D2 branch. A femoral artery was exposed on the left leg by incision and a catheter (Catheter 2) was inserted into that artery. Catheter 2 was attached to a withdrawal pump (model PHD 2000, Harvard Apparatus). All connecting lines and both catheters were primed with heparinized saline, and blood was collected at a rate of 4 mL/min over a four minute period, resulting in a 16 mL reference blood collection. Two standard IV ear catheters were placed in each ear of the pig (one for injecting the radiotracers of the present invention and the other one for injecting a stressing agent.)

Rest Study:

Five mL of thoroughly mixed gold BioPAL STERIspheres™ were injected into the left atrium of the pig via Catheter 1 over 10-30 seconds. The blood was then collected through Catheter 2 at a withdrawal rate of 4 mL/min for 4 minutes, resulting in a 16 mL reference blood collection. A solution of the mixture of compounds 6-9 for parenteral administration was prepared by diluting 0.20 mL of a 13.6 mCi/mL aqueous solution of the mixture of compounds 6-9 with 0.16 mL of 95% ethanol and 2.84 mL of 10 mM sodium acetate buffer, to produce 3.2 mL of a 0.85 mCi/mL solution in 5% ethanol. Three mL of the parenteral solution of the mixture of compounds 6-9 were injected into a standard IV ear catheter into the left ear of the pig after the blood was collected and an imaging session was started. Electrocardiogram-gated images of the distribution of I-123 were acquired on a dedicated cardiac SPECT camera (Discovery NM 530c, GE Healthcare) with the heart of the animal centered in the field-of-view of the camera. The dedicated system used pinhole collimation and 19.8 cm×8 cm cadmium-zinc-telluride solid state detectors. The sensitivity of the camera was ~4× that of a traditional gamma camera and it had a 2× improvement in energy resolution. The data were acquired simultaneously in list mode and using an energy window of 159±16 keV. Two acquisitions of 15 min duration each were obtained with the animal in a resting state, one immediately following the other, with the first starting immediately following injection of the tracer. A third 15 min resting image was obtained just prior to stressing the animal. All images were reconstructed as per a standard clinical protocol using a vendor-supplied iterative algorithm based on the maximum-likelihood expectation-maximization (MLEM) reconstruction algorithm. Data were not corrected for the effects of attenuation.

Stress Study:

The time line for the stress study was as described below:

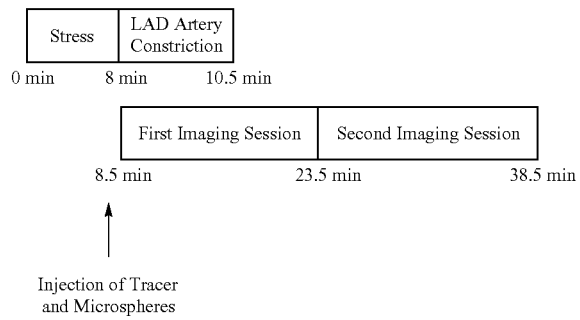

The animal was stressed using the vasodilating agent Persantine (dipyridamole), which was injected into the ear catheter of the right ear. Persantine (0.56 mg/kg/min) was delivered via IV infusion over 4 min. The LAD Coronary artery of the pig was constricted at the 8 minute period to emulate an ischemic condition in the pig. Samarium BioPAL STERIspheres™ were injected at time point 8:30 min after the start of Persantine infusion, to allow the blood pressure to stabilize. Five mL of thoroughly mixed samarium Biopal STERIspheres™ were injected into the left atrium via catheter 1 over 10-30 seconds. The blood was collected through Catheter 2 at a withdrawal rate of 4 mL/min for 4 min, resulting in a 16 mL reference blood collection. At the same time, 4 mL of a parenteral solution of the mixture of compounds 6-9 was injected into a standard IV ear catheter of the left ear and two imaging sessions of fifteen minutes were performed. The parenteral solution was prepared by diluting 0.55 mL of a 13.7 mCi/mL aqueous solution of the mixture of compounds 6-9 with 0.21 mL of 95% ethanol and 3.44 mL of 10 mM sodium acetate buffer, to produce 4.2 mL of a 1.8 mCi/mL solution of the mixture of compounds 6-9 in water.

Figure 6A:
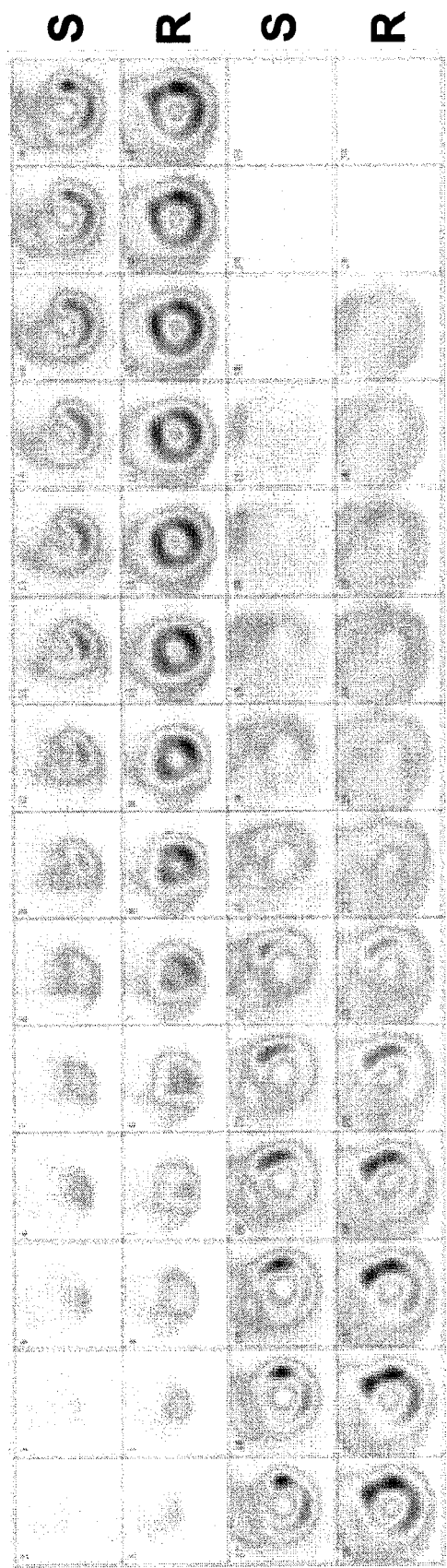
FIGS. 6A-C show short axis images, horizontal long axis images and vertical long axis images, respectively, of sections of the in vivo heart of a pig subject in a rest state (R) and a stressed state (S), which were determined by SPECT imaging. The light regions in FIGS. 6A-C are representative of areas of relatively lower uptake of the radio-labeled tracer of the present invention, and are indicative of areas of reduced blood flow (ischemia).
Figure 6B:
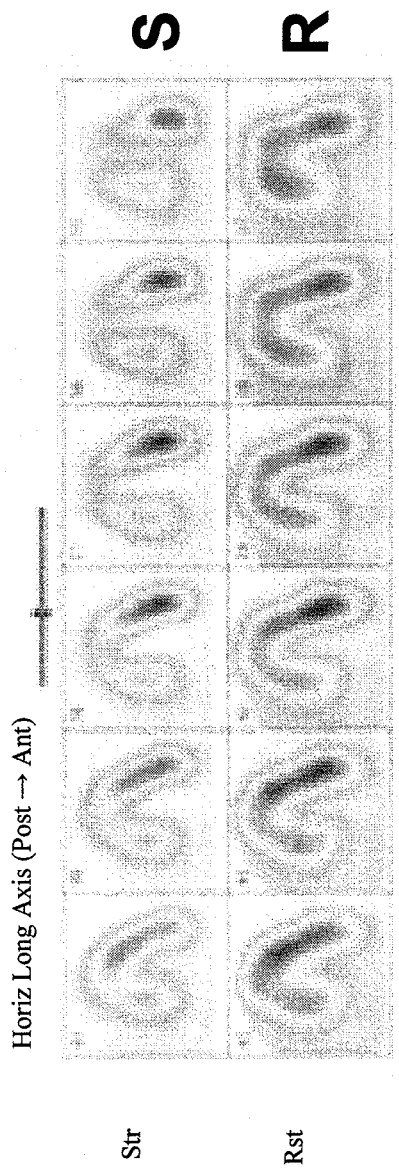
Figure 6C:
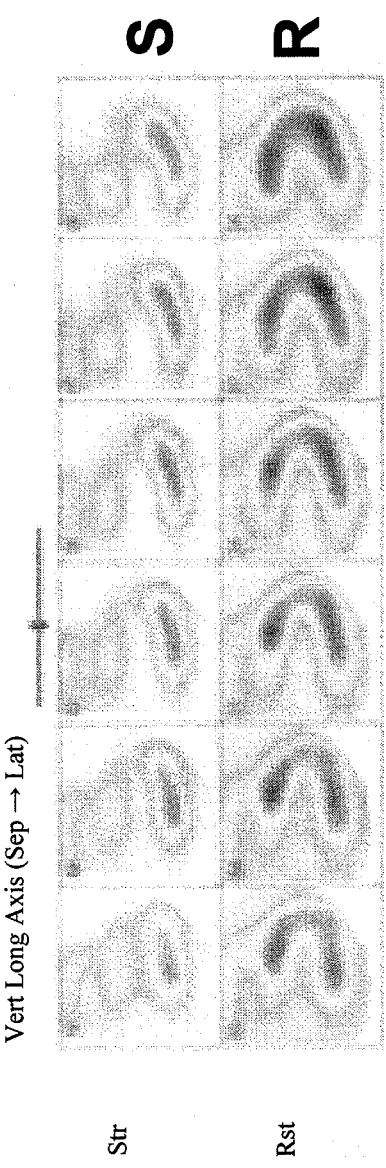
Figure 7A:
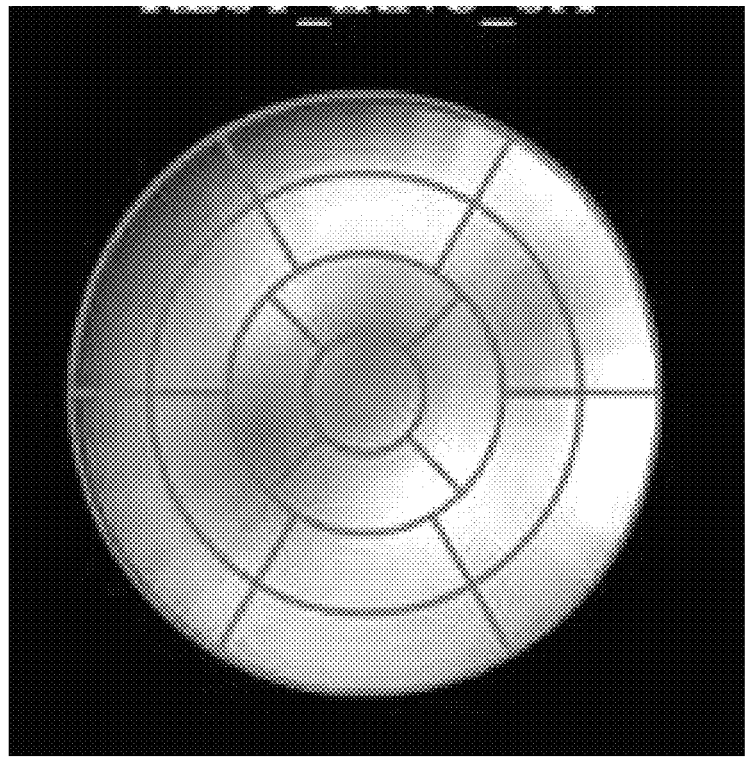
FIGS. 7A and 7B show polar maps determined by SPECT imaging of the gamma radiation emitted by a mixture of the [$^{123}$I] iodinated rotenone derivatives 6-9 in the in vivo heart of the pig subject in the resting state and stressed state, respectively.
Figure 7B:
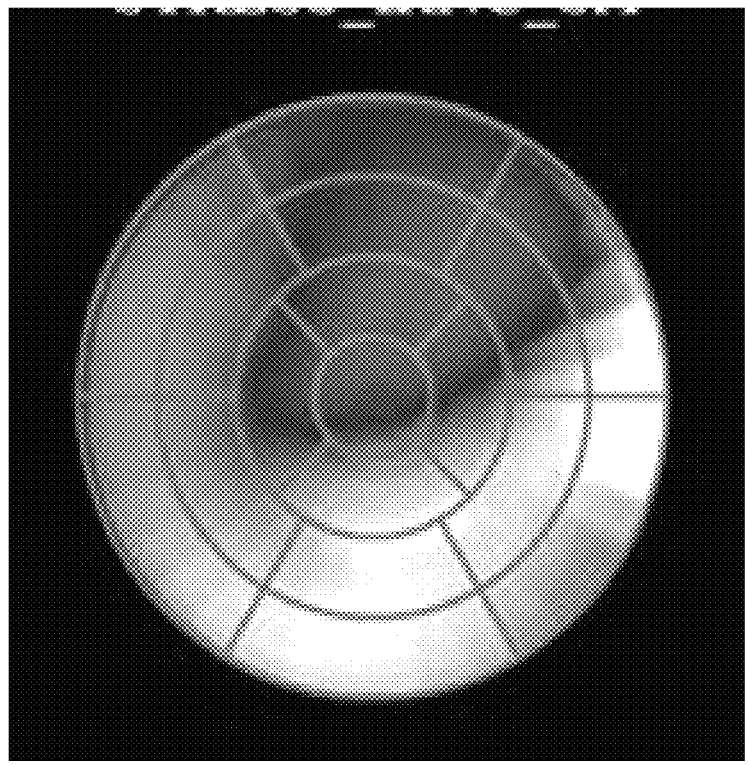

FIGS. 6A-C show short axis images, horizontal long axis images and vertical long axis images, respectively, of sections of the in vivo heart of a pig subject in rested (R) and stressed (S) states, which were determined by SPECT imaging. FIGS. 7A-B show polar maps of the in vivo heart of the pig subject in the resting state and the stressed state, respectively, which were prepared from the images obtained during the SPECT imaging sessions. The results of the SPECT imaging experiment were confirmed by two additional experiments involving direct measurements of gamma radiation emitted by the radio-iodinated rotenone derivatives of the present invention and by the gold and samarium microspheres following neutron activation in transected sections of the isolated heart of the pig subject.

After the images shown in FIGS. 7A-B were obtained, the pig was euthanized with a bolus injection of sodium pentobarbital (240 mg/ml) 2 mL/4.5 kg. The pig heart was harvested after euthanasia and rinsed thoroughly under running water. The left ventricle was isolated and cut into five transverse slices, which were further subdivided into transmural segments of about 1 gram, each containing approximately equal concentration of the endocardium and epicardium.

The tissue and blood samples were weighed and measured using a gamma well counter to determine the amount of gamma radiation emitted by the I-123 radiolabel of the radio-iodinated tracers of the present invention. The measured gamma radiation in each segment represents the combined amount of gamma radiation emitted by the tracers in that segment during the resting and stressed states of the heart. The counts and the weights of the samples were also used to calculate the percentage of injected dose per gram of tissue (% ID/g). After the I-123 in the blood and tissue samples had completely decayed, both the tissue and the blood were dried in an oven at 70° C. for 48-72 h, the samples were sent for neutron activation and the gamma radiation emitted by each of the resulting radioactive [$^{198}$Au]gold-containing microspheres and [$^{153}$Sm]samarium-containing microspheres, which were embedded in the samples, were measured. Polar maps of the resting and stressed states of the isolated heart of the pig were generated using MATLAB™ to assemble the gamma measurement results in all the transected segments from the bottom (apex) to the top (AV groove) of the pig heart.

The initial polar map generated from measurements of gamma radiation emitted by the radio-iodinated tracers of the present invention (not shown) represented a combined polar map of the distribution of gamma radiation in the isolated heart of the pig in both the resting and stressed states. To remove the contribution of the distribution of gamma radiation in the pig heart during the resting state from the combined polar map, the value of this contribution was first determined from the SPECT images of the in vivo pig heart.

During the acquisition of the SPECT images (FIGS. 6A-C), both a polar map at rest and a polar map following the induction of stress were obtained. The initial polar map that was generated on the basis of images acquired after the induction of stress contained residual activity from the resting state, and, therefore, approximately represented an initial combined polar map of both the resting and stressed states of the in vivo pig heart. The contribution of the resting state polar map was removed from the combined polar map by aligning these two polar maps and then subtracting the contribution of each pixel value of the resting state polar map from each corresponding pixel value of the initial combined polar map to provide a corrected polar map approximately representing the polar map of the stressed state of the in vivo pig heart. This procedure provided two separate matrices of pixel values representing the fractions of the pixel values of the initial combined polar map corresponding to the pixel values of the resting state polar map and the stressed state polar map of the pig heart.

The matrices obtained from the analysis of the SPECT polar maps were used to separate the combined resting state and stressed state polar map obtained from direct measurement of gamma radiation emitted from the radio-iodinated rotenone derivatives into individual resting state and stressed state polar maps.

Figure 7C:
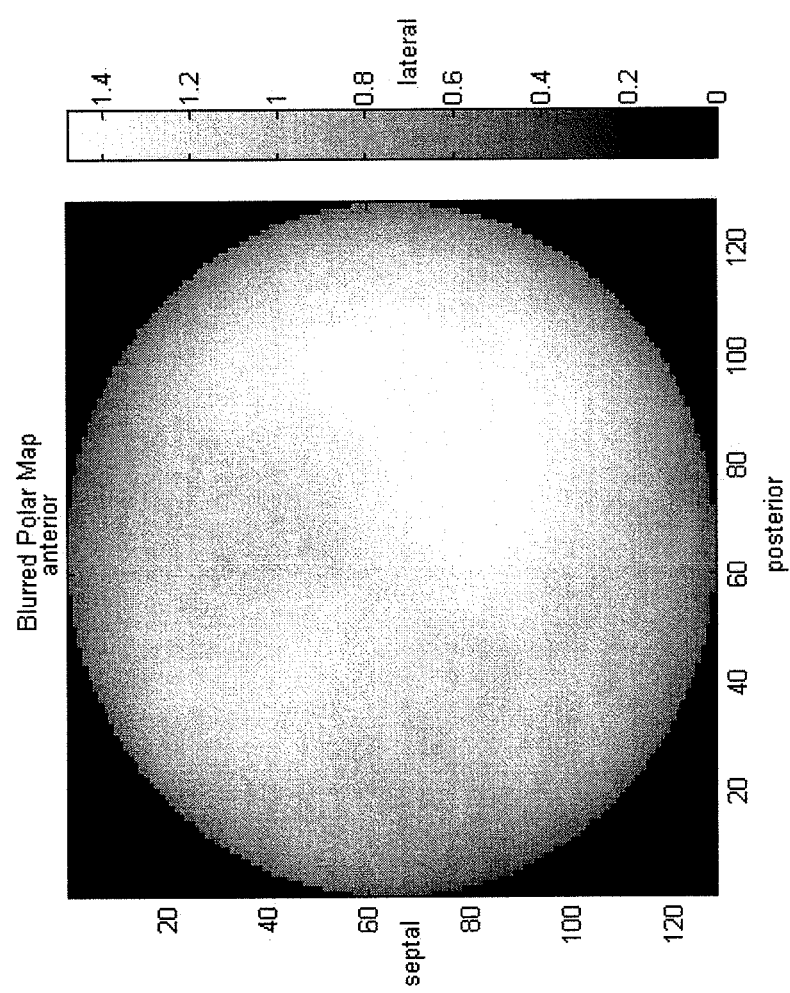
FIGS. 7C and 7D show the polar maps determined using measurements of the gamma radiation emitted by neutron-activated gold and samarium BioPal STERIspheres™, which were introduced into the heart of the pig subject in the resting state and stressed state, respectively.
Figure 7D:
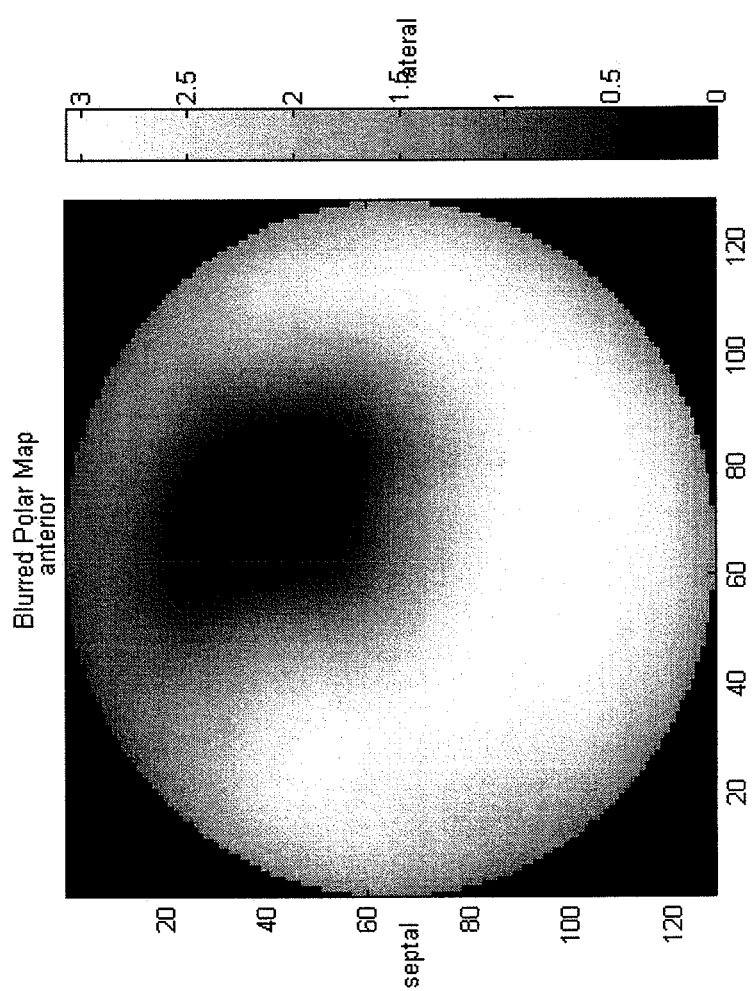
Figure 7E:
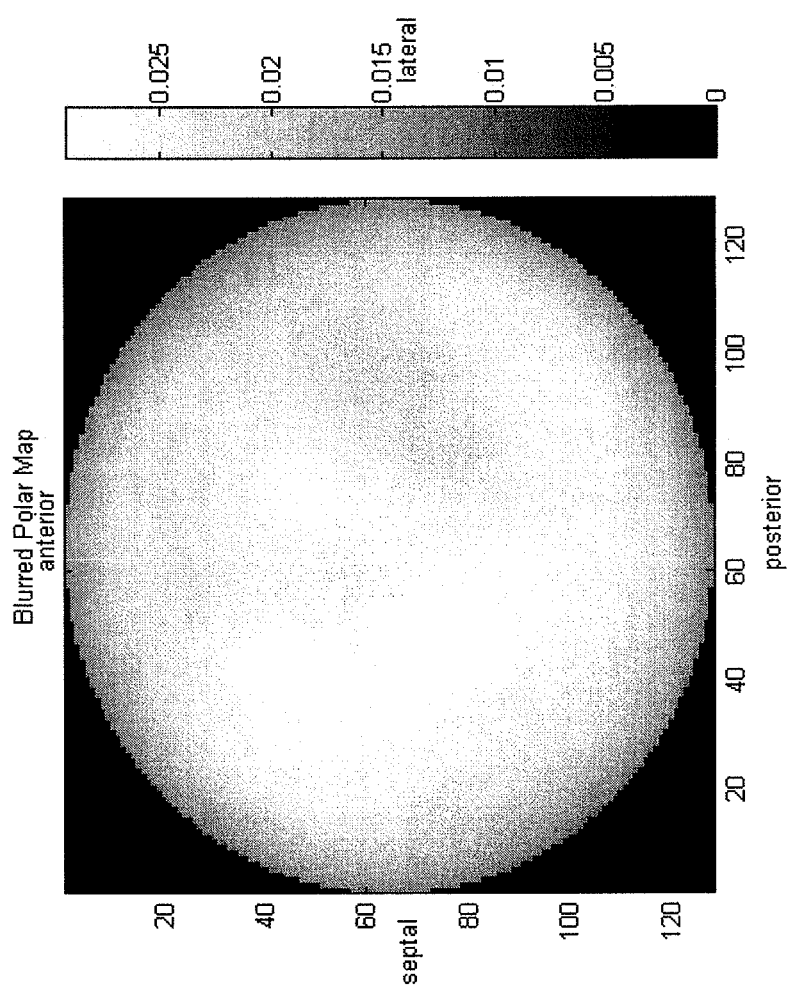
FIGS. 7E and 7F show the polar maps determined using measurements of the gamma radiation emitted by a mixture of the [$^{123}$I] iodinated rotenone derivatives 6-9 in the heart of the pig subject in the resting state and stressed state, respectively. The dark regions in FIGS. 7B, 7D and 7F are indicative of areas of reduced blood flow (ischemia).
Figure 7F:
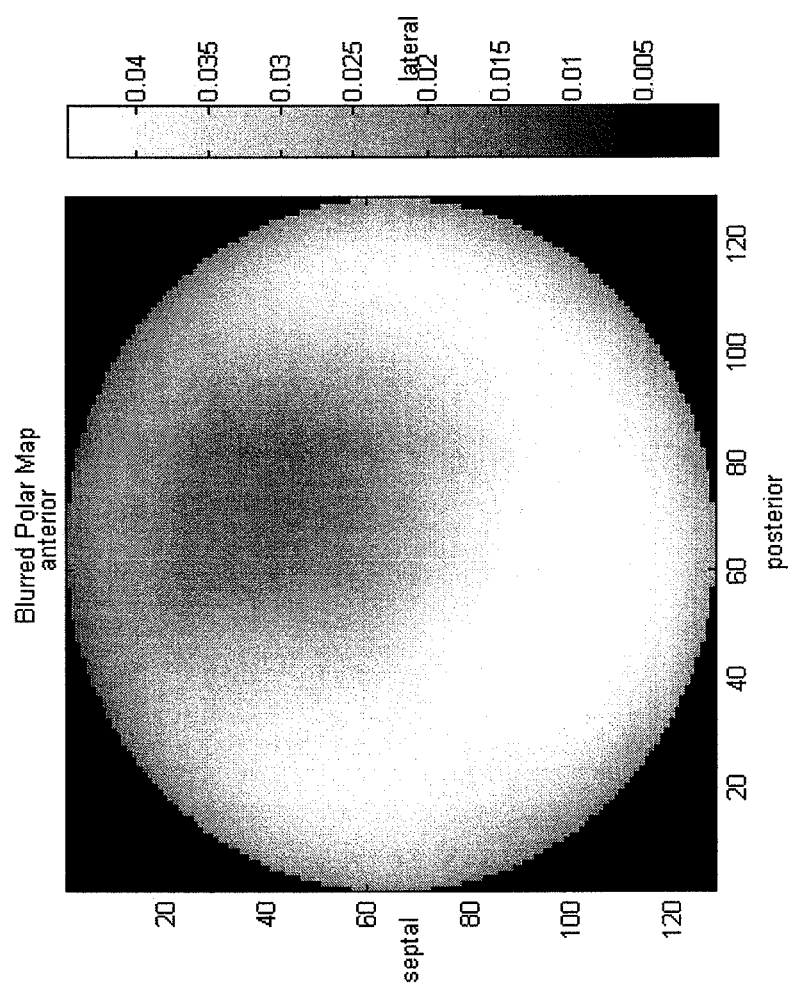

FIGS. 7C and 7D show the polar maps determined by measurement using the gamma radiation emitted by the gold and samarium BioPal STERIspheres™ in the heart of the pig subject in the resting and stressed states, respectively, following neutron activation. FIGS. 7E and 7F show the polar maps determined by measurement using the gamma radiation emitted by the [$^{123}$I] iodinated rotenone derivatives in the heart of the pig subject in the resting state and the stressed state (after removing the contribution of the resting state), respectively.

The dark regions shown in FIGS. 7B, 7D and 7F are indicative of reduced blood flow in the pig heart under stress conditions as a result of the induced occlusion caused by constriction of the LAD coronary artery. The position of reduced blood flow aligns with the position of constriction in the heart. In contrast, blood flow in the pig heart under rest conditions is substantially uniform throughout the heart as shown by FIGS. 7A, 7C and 7E. The contrast observed with the microspheres are greater than that observed with the radiotracers of the present invention possibly due to a larger amount of the microspheres being blocked in the capillaries of the heart than the amount of the radiotracers taken up by the myocardial cells of the heart. These results indicate that the radiotracers of the present invention can be used in myocardial imaging of subjects having ischemia.

Determination of Uptake of the Radiotracers of the Present Invention as a Function of Myocardial Blood Flow (MBF)

The myocardial blood flow (MBF) that was present in the tissue samples during the resting and stressed states was determined from the total amount of gamma radiation emitted from each of the radioactive gold and samarium microspheres, respectively, in the isolated transections of the heart of the pig and the dried blood sample according to the following equation:

MBF=[(Reference blood sample withdrawal rate (4 mL/min)/(Weight of myocardial sample (g)]×[Isotope count (myocardial sample)/Isotope counts (reference blood sample)].

Figure 8:
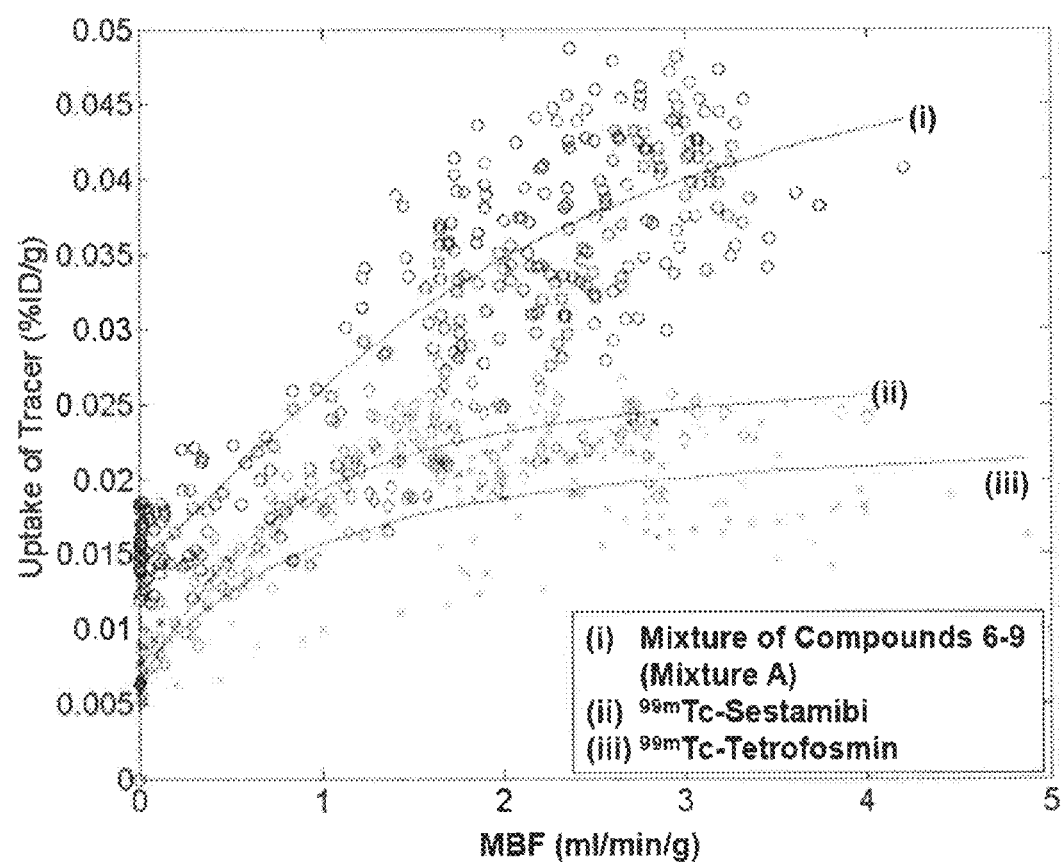
FIG. 8 shows a plot of uptake (percent injected dose per gram; % ID/g) of a mixture of [$^{123}$I] iodinated rotenone derivatives 6-9 of the present invention, Myoview™ ($^{99m}$Tc-tetrofosmin) and $^{99m}$Tc-sestamibi in the hearts of pig subjects as a function of myocardial blood flow (MBF).

FIG. 8 illustrates a plot of uptake (percent of injected dose per gram of tissue; % ID/g) of the radiotracer compounds of the present invention as a function of the myocardial blood flow in the pig heart under stress and induced ischemic conditions as determined using the marked microspheres. This data demonstrate that the uptake of the mixture of compounds 6-9 of the present invention only begins to level off (roll off) at a myocardial flow rate of 3 ml/min/g at two hours after injection, while the Myoview product (Technetium ($^{99m}$Tc) tetrofosmin) and Tc-99m-Sestamibi begin to roll off at a rate of 2 ml/min/g and 1.5 mL/min/g, respectively, at two hours after injection.

The slopes of the non-linear fitted lines to the data for the isomers of Mixture A and $^{99m}$Tc-sestamibi are shown in FIG. 8 are −3.60 and −1.21, respectively.

FIG. 3 of Broisat et al. (A. Broisat, M. Ruiz, N.C. Goodman, S. M. Hanrahan, B. W. Reutter, K. M. Brennan, M. Janabi, S. Schaefer, D. D. Watson, G. A. Beller, H. F. VanBrocklin, and D. K. Glover Circ Cardiovasc Imaging 2011; 4:685-692, the disclosure of which is incorporated by reference herein) shows uptake data for 7-(Z)-[$^{123}$I]iodorotenone ($^{123}$I-ZIROT) plotted as a function of microsphere flow (ml/min/g) from a representative dog having a critical LAD coronary artery stenosis that received intravenous adenosine. The slope of a non-linear fitted line to the $^{123}$I-ZIROT data shown in FIG. 3 of Broisat et al. is −3.59.

FIG. 4 of Glover et al. (D. K. Glover, M. Ruiz, N.C. Edwards, M. Cunningham, J. P. Simanis, W. H. Smith, D. D. Watson, G. A. Beller *Circulation* 1995; 91: 813-820, the disclosure of which is incorporated by reference herein) shows uptake data (activity (% normal)) for $^{99m}$Tc-Sestamibi plotted as a function of microsphere flow (ml/min/g) from a representative dog having a critical LAD coronary artery stenosis that received intravenous adenosine. The value of slope of −143 of the non-linear fitted line to the $^{99m}$Tc-Sestamibi data shown in FIG. 4 of Glover et al. was standardized to match the magnitude of the slope of the fitted line to the $^{123}$I-ZIROT data shown in FIG. 3 of Broisat et al by dividing that value by 100 to produce a comparable value of slope of −1.43.

The value of the ratio of the slope of the non-linear fitted line to the $^{123}$I-ZIROT data of Broisat et al. and the slope derived from the slope of the non-linear fitted line to the $^{99m}$Tc-Sestamibi data of Glover et al. is 2.5, while the value of the ratio of the slopes of the non-linear fitted lines to the data for Mixture A and $^{99m}$Tc-sestamibi shown in FIG. 8 of the present application is 3.0. These values suggest that the isomers of Mixture A have a similar rate of uptake with increasing flow to that of $^{123}$I-ZIROT.

The polar maps shown in FIG. 7 and the data illustrated in FIG. 8 suggest that compounds 6-9 of the present invention can be retained in the myocardium of a test subject at the relatively high myocardial flow rates resulting during the stress component of a myocardial perfusion imaging test, and would therefore be effective in diagnosing an ischemic condition in the subject.

Myocardial Distribution of Compounds 6-9

Preparation of retrograde perfusion (Langendorff) was performed as previously described (R. C. Marshall, P. Powers-Risius, B. W. Reutter, S. E. Taylor, H. F. VanBrocklin, R. H. Huesman, T. F. Budinger *J Nucl Med.* 2001; 42:272-281, which is incorporated by reference herein) using hearts from 1.5-2.5 kg male New Zealand White rabbits (Charles River, Wilmington Mass.). Following an injection of heparin (5 mg/kg) and median sternotomy, hearts were excised keeping the ascending aorta and aortic branches, lungs and thymus intact. The hearts were immediately placed into an ice-cold bath containing modified Tyrode's solution (10 mM NaCl, 1 mM $MgCl_2$, 28 mM $NaHCO_3$, 0.44 mM $NaH_2PO_4$, 2.5 mM $CaCl_2$, 6 mM KCl, 5 mM glucose, 100 mM sodium pyruvate with 22 g/L BSA and aerated with 95% $O_2$/5% $CO_2$) and thymus and fatty tissue were quickly removed. The hearts were then suspended on an aortic cannula and perfused with pre-warmed modified Tyrode's buffer through a water jacketed, temperature regulated Langendorff perfusion system (Radnotti, Calif., USA) at a constant flow rate. Total time for suspension onto the Langendorff apparatus was typically 60 seconds or less. Following suspension on the aortic cannula, the remaining lung, trachea and extraneous tissues were removed.

Fluid from Thebesian circulation was drained via a polyethylene catheterized apical drain. A fluid filled latex ballon connected to a pressure transducer (Radnotti) was inserted into the left ventrical via the left atrium and mitral valve. Following excision of the right atrium, a pacing electrode (Radnotti) was placed at the level of the atria to allow controlled pacing of the heart.

Following final preparation, the left ventricular balloon was inflated to achieve an end-diastolic pressure of approximately 8-10 mmHg with a constant systolic pressure held between 60-80 mm Hg. The heart was continually perfused with modified Tyrode's solution warmed to 38° C. and was held in an enclosed chamber to maintain humidity and temperature. The heart was paced with a Grass SD9 stimulator (Harvard Apparatus, Montreal QC) at 180 beats per minute with a stimulus of 4 V delivered over 4 ms. Perfusion and ventricular pressures were monitored throughout the experiment using a BioPac data acquisition system (BioPac, Montreal QC). Hearts that displayed irregular pressures and electrical activity during the experiment were not included in the analyses.

After stabilization (approximately 15-30 minutes), 5 second samples were collected for 15-20 seconds representing baseline activity after which a 200 μL bolus injection of radiotracer (2 μCi $^{131}$I-albumin, $^{99m}$Tc-sestamibi, $^{201}$Tl or a mixture of compounds 6-9 (Mixture A: composition comprising isomeric mixture of 12% 6 and 7 diastereomers; 88% 8 and 9 diastereomers) was injected via an injection port positioned immediately above the aortic cannula. Five second venous effluent samples were collected continuously for the first 5 minutes, at 30 second intervals for the next 10 minutes and every 60 seconds for 20 minutes thereafter into pre-weighed vials. Radioactivity from all samples were counted in a gamma counter and data was analyzed using Matlab software. The average venous appearance rates for each tracer was determined for $^{131}$I-albumin (N=3), $^{99m}$Tc-sestamibi (N=5), Mixture A (N=6) and $^{201}$Tl (N=6) collected at a flow rate of 1.7 ml/min/g LV wet weight. Maximal uptake values were determined for $^{99m}$Tc-sestamibi and Mixture A at varying flow rates (0.35-3.1 ml/min/g LV wet weight).

Figure 9:
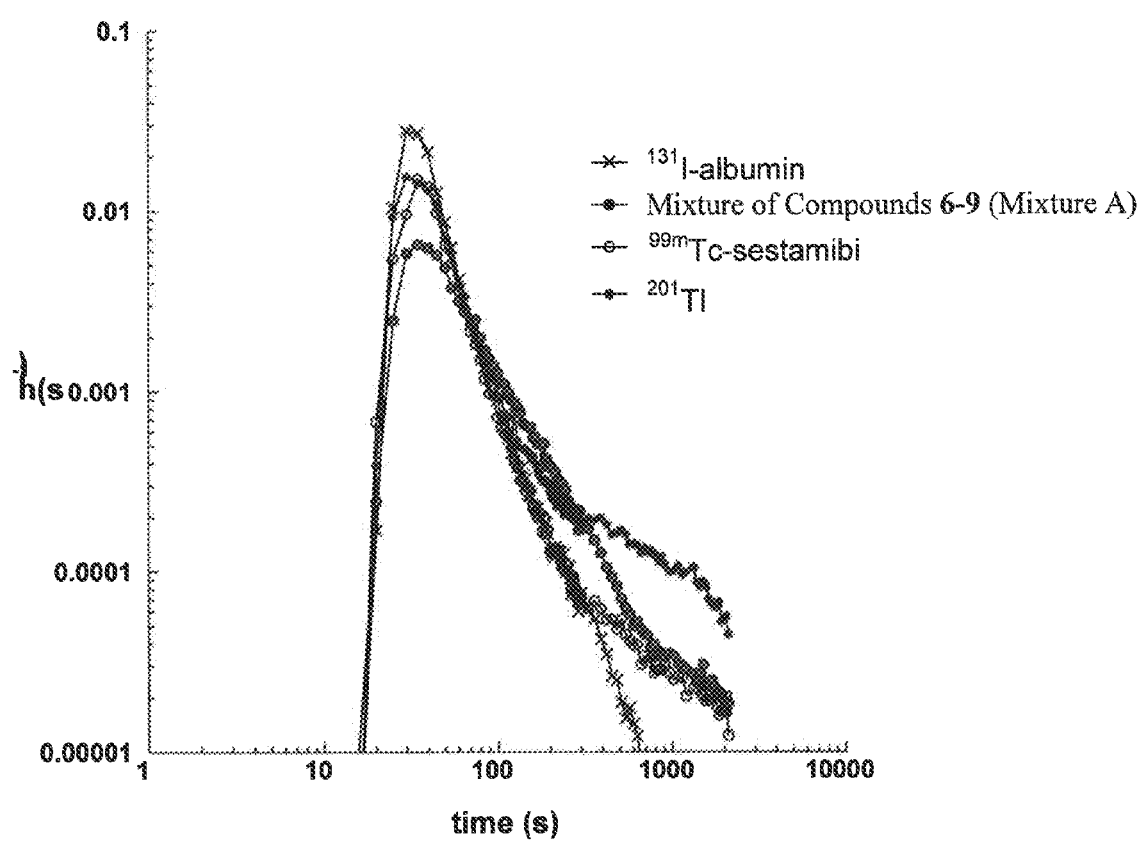
FIG. 9 shows the values of the fractional venous appearance rates $h(s^{-1})$ of $^{131}$I-albumin, $^{99m}$Tc-sestamibi $^{201}$Thallium and a mixture of [$^{123}$I] iodinated rotenone derivatives 6-9 of the present invention as a function of venous collection time at a flow rate of 1.7 ml/min/g LV.

Results:

From FIG. 9, the initial peak fractional venous appearance rates for the reference tracer ($^{131}$I-albumin) vs the perfusion tracers ($^{99m}$Tc-sestamibi and the isomers of Mixture A) can be qualitatively evaluated. The higher venous effluent rate observed with albumin (non-diffusable tracer) suggests that it remains in the intravascular space and does not perfuse into the myocardium, i.e. extravascular space. Conversely, the diffusible tracers, $^{99m}$Tc-sestamibi, $^{201}$Tl and the isomers of Mixture A have lower fractional venous appearance rates suggesting that these tracers escape from the vasculature into the extravascular space and perfuse the myocardium. At later time points, $^{99m}$Tc-sestamibi, $^{201}$Tl and the isomers of Mixture A have higher fractional appearance rates signifying that they re-enter the vasculature and exit the myocardium through the venous effluent. The lower peak venous effluent rate observed with the isomers of Mixture A suggests a longer myocardial retention relative to $^{99m}$Tc-sestamibi, $^{201}$Tl and $^{131}$I-albumin.

In comparison with Marshall et al., the curves for $^{99m}$Tc-sestamibi and $^{131}$I-albumin are very similar. The isomers of Mixture A have a comparable venous appearance rate to 7'-Z-[$^{125}$I]iodorotenone ($^{125}$I-rotenone) in the early portions of the curve (compare FIG. 1, Marshall et al. 2001 with FIG. 9 of the present application). At the later portions of the curve, $^{125}$I-rotenone appears to have a higher venous effluent rate relative to the isomers of Mixture A. This implies that following myocardial perfusion into the extravascular space, the isomers of Mixture A exit the myocardium more slowly than $^{125}$I-rotenone. A slower myocardial exit is beneficial for clinical diagnostic imaging since this permits the physician to gather images over a longer period of time thereby increasing image resolution, sensitivity and quality.

Maximal tracer uptake U(t) is a measure of the maximum content of tracer remaining in the myocardium relative to the total amount injected. Six animals for each tracer were perfused at varying flow rates (expressed as mL/min/g left ventricular wet weight). The overall maximal uptake of the isomers of Mixture A was significantly greater than $^{99m}$Tc-sestamibi (P=0.03). Additionally, the rate of increase in uptake with increasing flow was significantly greater for the isomers of Mixture A than sestamibi (P=0.007). The results from linear regression for the isomers of Mixture A are y=0.86x+0.26, $R^2$=0.92 and for sestamibi are y=0.33x+0.14, $R^2$=0.88.

Figure 10:
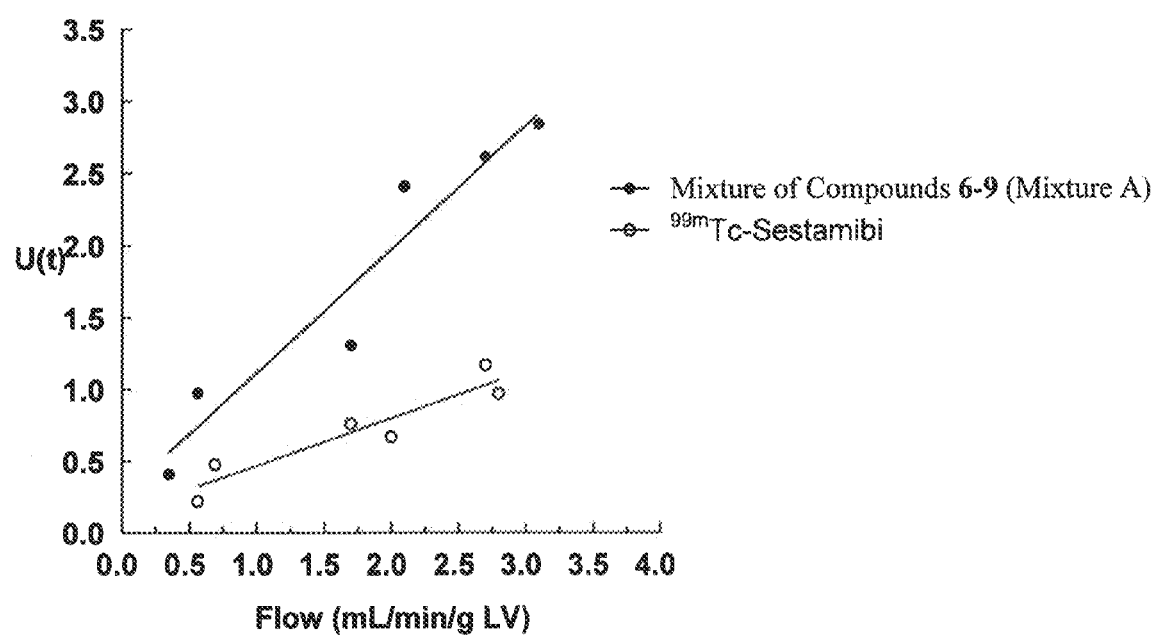
FIG. 10 shows the values of the maximum net uptake of $^{99m}$Tc-sestamibi and a mixture of [$^{123}$I] iodinated rotenone derivatives 6-9 of the present invention. Each point represents a single experiment from a separate animal.

Qualitatively, the maximum net uptake for $^{99m}$Tc-sestamibi and the isomers of Mixture A shown in FIG. 10 is similar to that reported for $^{125}$I-rotenone and $^{99m}$Tc-sestamibi in Marshall et al., (2001) (compare FIG. 6A of Marshall et al. with FIG. 10 of the present application). The correlation coefficients for Mixture A (r=0.96) and $^{99m}$Tc-sestamibi (r=0.94) suggest that in these experiments tracer uptake is highly correlated to flow rate.

Marshall et al. report slopes of 0.29 and 0.78 for the fitted linear lines to the maximal uptake data for $^{99m}$Tc-sestamibi and $^{125}$I-rotenone, respectively. The slopes of the fitted lines to the data for $^{99m}$Tc-sestamibi and the isomers of Mixture A shown in FIG. 10 of the present application are 0.33 and 0.86, respectively. The value of the ratio of the slopes of the fitted lines for $^{125}$I-rotenone and $^{99m}$Tc-sestamibi from Marshall et al. is 2.69, while the value of the ratio of the slopes of the fitted lines for Mixture A and $^{99m}$Tc-sestamibi shown in FIG. 10 is 2.61. These values suggest that the isomers of Mixture A have a similar rate of uptake with increasing flow to that of $^{125}$I-rotenone. A linear uptake of tracer with increasing flow is especially desired in a clinical setting since in patients, deficiencies in myocardial perfusion are almost exclusively detected at higher blood flow rates, i.e. during a stress test by comparison of low (ischemic) and high flow (normal) areas.

One or more currently preferred embodiments have been described by way of example. It will be apparent to persons skilled in the art that a number of variations and modifications can be made without departing from the scope of the invention as defined in the claims.

What is claimed is:

1. A compound of formula (I) or (II):

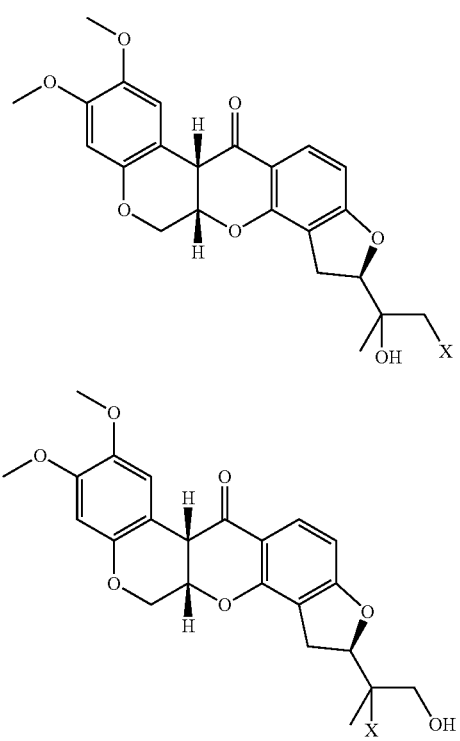

wherein X is a gamma-emitting radionuclide selected from the group consisting of $^{123}$I, $^{124}$I, $^{125}$I and $^{131}$I.

2. The compound according to claim 1, wherein X is $^{123}$I, $^{125}$I or $^{131}$I.

3. The compound according to claim 1, wherein the compound is of the formula (Ia):

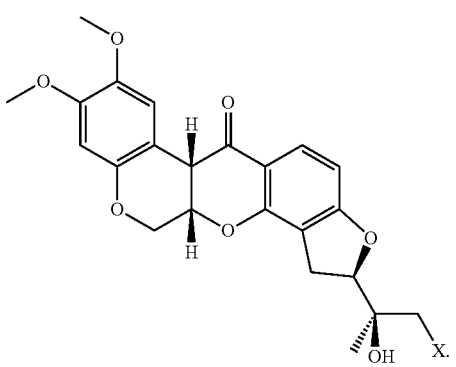

4. The compound according to claim 1, wherein the compound is of the formula (Ib):

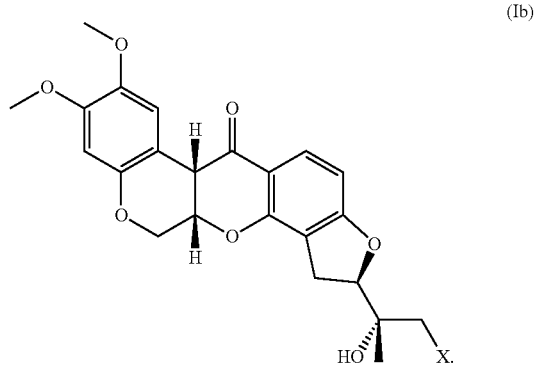

5. The compound according to claim 1, wherein the compound is of the formula (IIa):

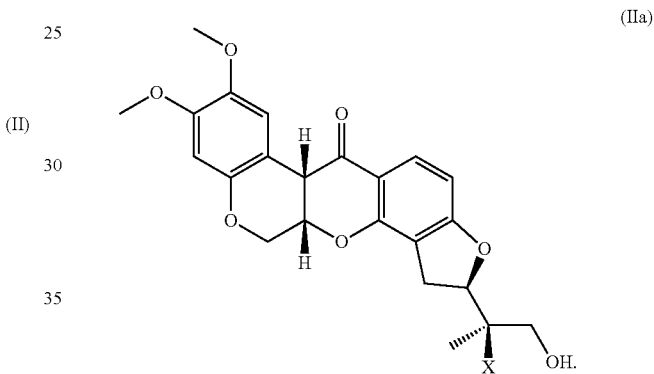

6. The compound according to claim 1, wherein the compound is of the formula (IIb):

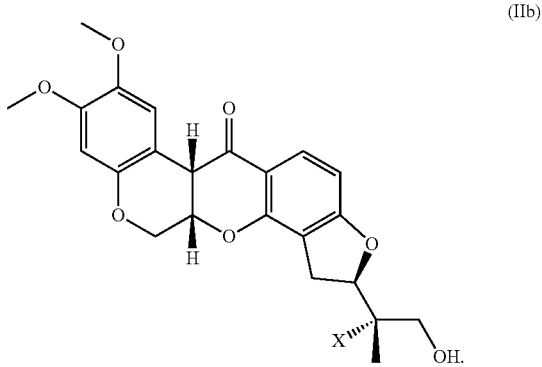

7. A pharmaceutical composition comprising a compound of formula (I), a compound of formula (II), or a mixture thereof:

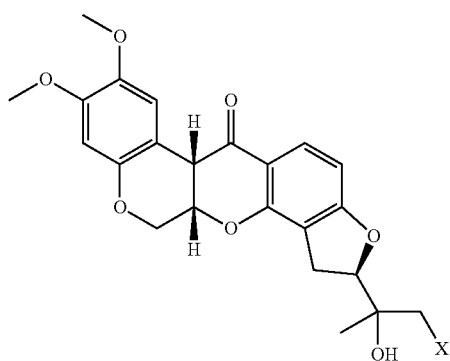
(I)

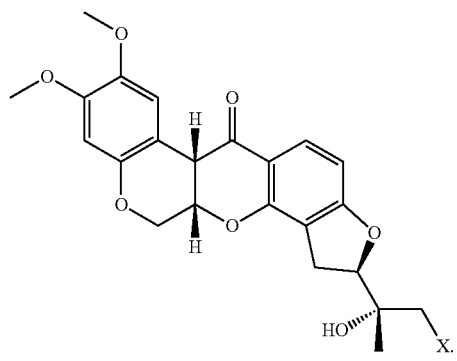
(Ib)

10. The pharmaceutical composition according to claim 7, wherein the compound is of the formula (IIa):

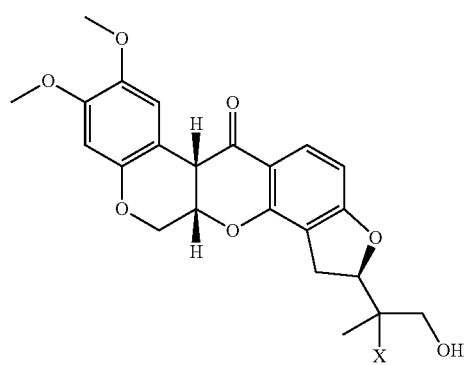
(II)

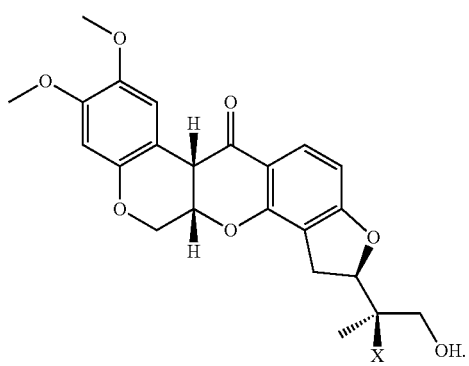
(IIa)

wherein X is a gamma-emitting radionuclide selected from the group consisting of $^{123}$I, $^{124}$I, $^{125}$I and $^{131}$I, and a physiologically acceptable vehicle.

8. The pharmaceutical composition according to claim 7, wherein the compound is of the formula (Ia):

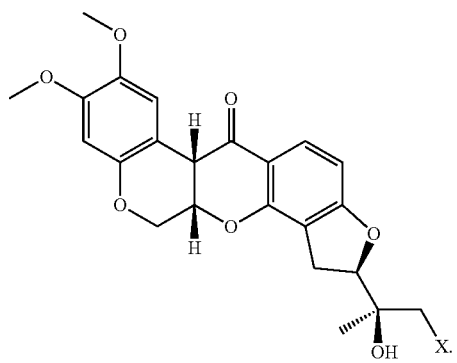
(Ia)

9. The pharmaceutical composition according to claim 7, wherein the compound is of the formula (Ib):

11. The pharmaceutical composition according to claim 7, wherein the compound is of the formula (IIb):

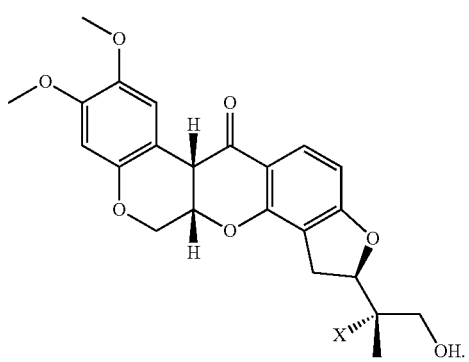
(IIb)

12. The pharmaceutical composition according to claim 7, wherein the pharmaceutical composition comprises a mixture of two or more of a compound of formula (Ia), a compound of formula (Ib), a compound of formula (IIa), and a compound of formula (IIb):

(Ia)

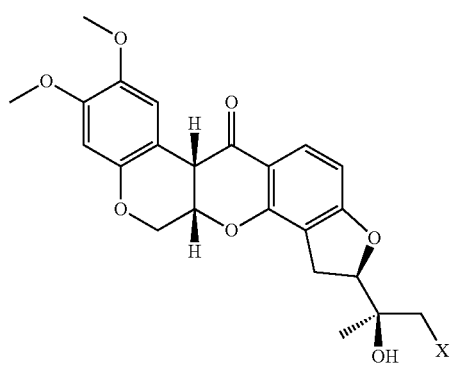

(Ib)

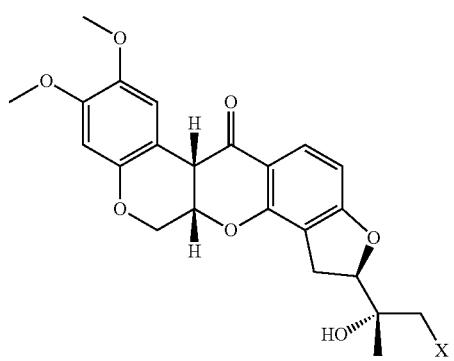

(IIa)

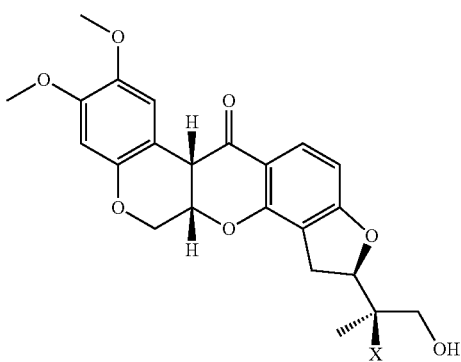

(IIb)

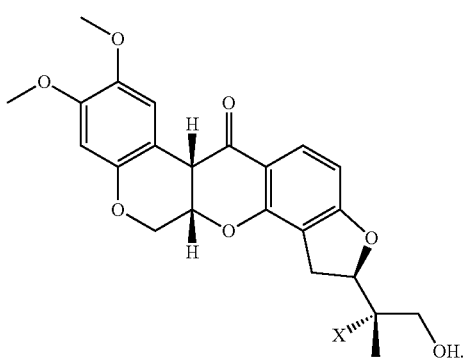

13. The pharmaceutical composition according to claim 7, wherein X is $^{123}$I, $^{125}$I or $^{131}$I.

14. A method of imaging a region in a patient, comprising: administering to the patient a diagnostically effective amount of a pharmaceutical composition comprising a compound of formula (I), a compound of formula (II), or a mixture thereof:

(I)

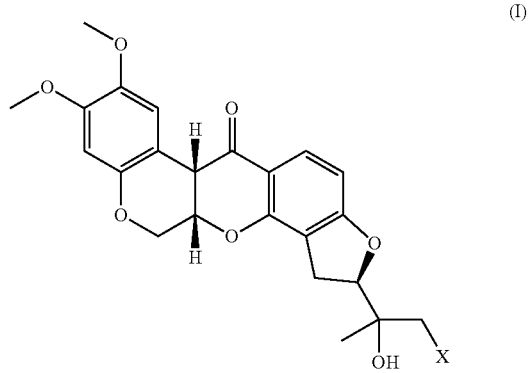

(II)

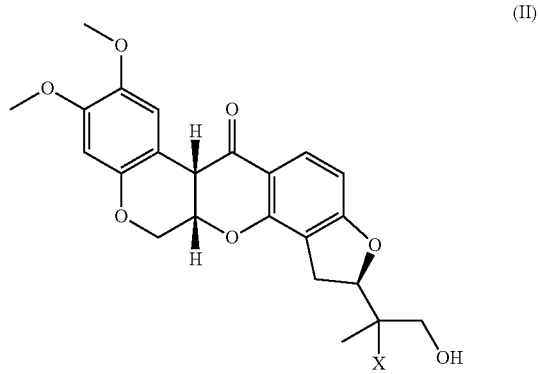

wherein X is a gamma-emitting radionuclide selected from the group consisting of $^{123}$I, $^{124}$I, and $^{131}$I, and a physiologically acceptable vehicle, a portion of the composition being retained in the region of the patient,
detecting radiation in the region of the patient, and
obtaining an image of the region of the patient.

15. The method according to claim 14, wherein the compound is of the formula (Ia):

(Ia)

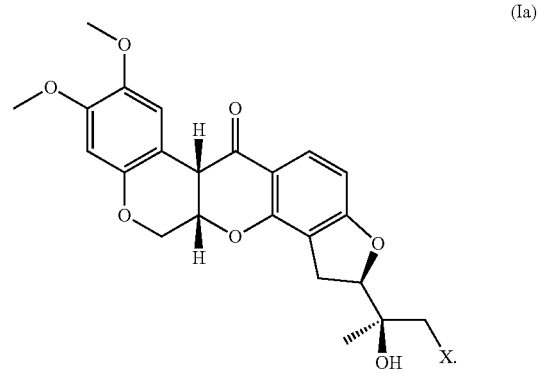

16. The method according to claim 14, wherein the compound is of the formula (Ib):

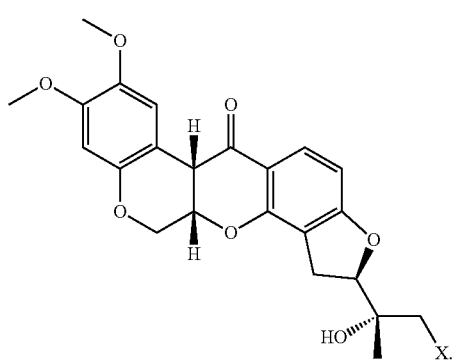
(Ib)

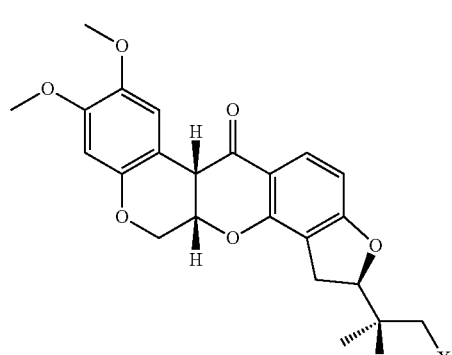
(Ia)

17. The method according to claim 14, wherein the compound is of the formula (IIa):

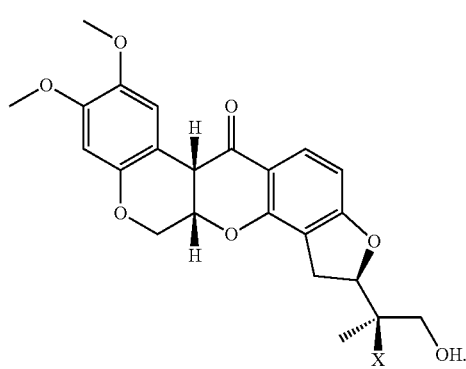
(IIa)

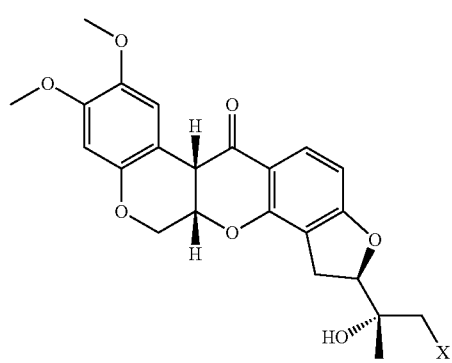
(Ib)

(IIa)

18. The method according to claim 14, wherein the compound is of the formula (IIb):

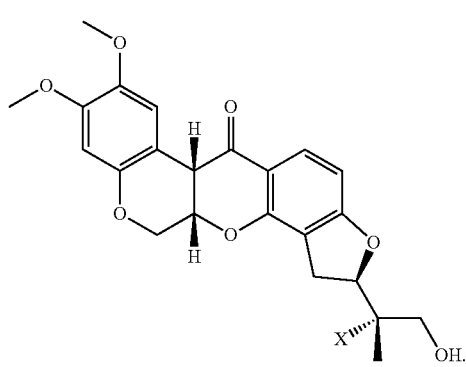
(IIb)

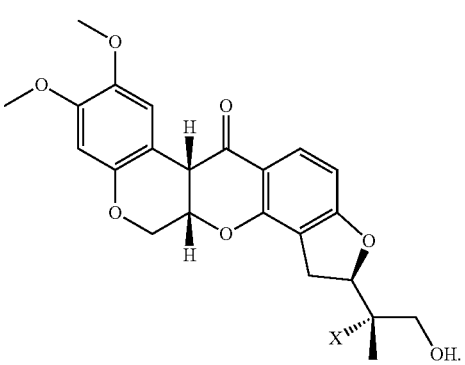
(IIb)

19. The method according to claim 14, wherein the pharmaceutical composition comprises a mixture of two or more of a compound of formula (Ia), a compound of formula (Ib), a compound of formula (IIa), and a compound of formula (IIb):

20. The method according to claim 14, wherein X is $^{123}$I, $^{125}$I or $^{131}$I.

21. The method according to claim 14, wherein the region of the patient is the heart.

22. The method according to claim 21, wherein prior to the step of administering, stress is induced in the patient.

23. The method according to claim 22, wherein the stress is induced in the patient for a period of about 1 to about 8 minutes.

24. The method according to claim 22, wherein the compound of formula (I) is administered to the patient 30 seconds to 1 minute after the period in which stress has been induced in the subject.

25. The compound according to claim 1, wherein the compound is selected from the group consisting of:

(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((S)-2-hydroxy-1-[$^{124}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-1-[$^{124}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((S)-2-hydroxy-1-[$^{125}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-1-[$^{125}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((S)-2-hydroxy-1-[$^{131}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-1-[$^{131}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one;

(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-[$^{124}$I]iodo-1-hydroxypropan-2-yl)-8,9-dimethoxy-1,2,12,12a-tetrahydrochromeno[3,4-b]furo[2,3-h]chromen-6(6aH)-one;

(2R,6aS,12aS)-2-((S)-2-[$^{124}$I]iodo-1-hydroxypropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-[$^{125}$I]iodo-1-hydroxypropan-2-yl)-8,9-dimethoxy-1,2,12,12a-tetrahydrochromeno[3,4-b]furo[2,3-h]chromen-6(6aH)-one;

(2R,6aS,12aS)-2-((S)-2-[$^{125}$I]iodo-1-hydroxypropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-[$^{131}$I]iodo-1-hydroxypropan-2-yl)-8,9-dimethoxy-1,2,12,12a-tetrahydrochromeno[3,4-b]furo[2,3-h]chromen-6(6aH)-one, and (2R,6aS,12aS)-2-((S)-2-[$^{131}$I]iodo-1-hydroxypropan-2-yl)-8,9-dimethoxy-1,2,12,12a-tetrahydrochromeno[3,4-b]furo[2,3-h]chromen-6(6aH)-one.

26. The pharmaceutical composition according to claim 7, wherein the composition comprises two or more of the compounds of formulas (Ia), (Ib), (IIa) and (IIb):

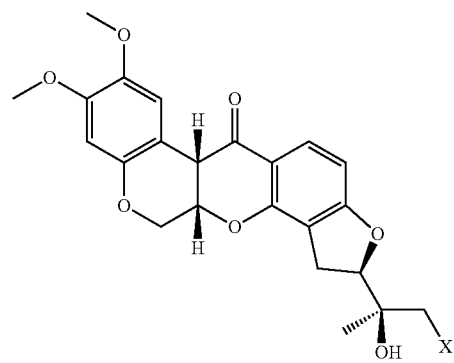
(Ia)

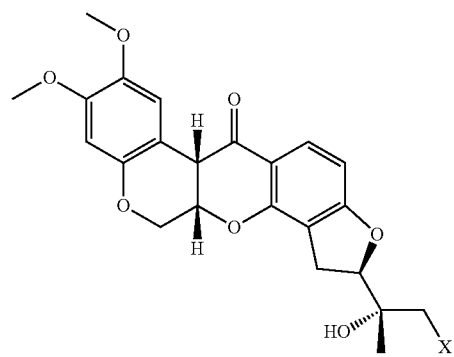
(Ib)

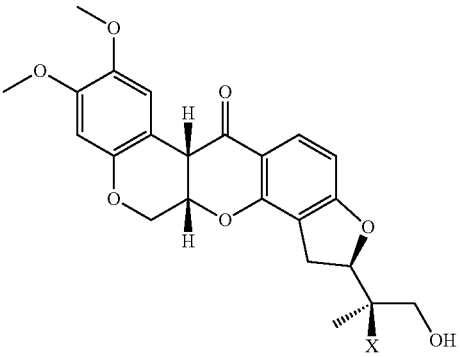
(IIa)

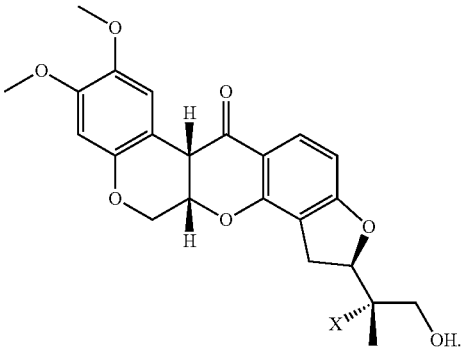
(IIb)

27. The compound according to claim 25, wherein the compound is selected from the group consisting of:

(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;

(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

28. The pharmaceutical composition according to claim 7, wherein the compound is one or more than one compound selected from the group consisting of:
(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

29. The method according to claim 14, wherein the compound is one or more than one compound selected from the group consisting of:
(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

30. The composition according to claim 26, wherein the composition comprises two or more compounds selected from the group consisting of:
(2R,6aS,12aS)-2-((S)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-hydroxy-1-[$^{123}$I]iodopropan-2-yl)-8,9-dimethoxy-1,2,12,12a-tetrahydrochromeno[3,4-b]furo[2,3-h]chromen-6(6aH)-one;
(2R,6aS,12aS)-2-((R)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one, and
(2R,6aS,12aS)-2-((S)-2-[$^{123}$I]iodo-1-hydroxypropan-2-yl)-8,9-dimethoxy-1,2,12,12a-tetrahydrochromeno[3,4-b]furo[2,3-h]chromen-6(6aH)-one.

* * * * *